(12) United States Patent
Hwang

(10) Patent No.: US 9,855,117 B2
(45) Date of Patent: Jan. 2, 2018

(54) TOOTH IMPLANT

(71) Applicant: P&N BIO CO., LTD., Seoul (KR)

(72) Inventor: Jeong Bin Hwang, Seoul (KR)

(73) Assignee: P&N BIO CO., LTD., Seoul (KR)

(*) Notice: Subject to any disclaimer, the term of this patent is extended or adjusted under 35 U.S.C. 154(b) by 252 days.

(21) Appl. No.: 14/394,962

(22) PCT Filed: Mar. 29, 2013

(86) PCT No.: PCT/KR2013/002621
§ 371 (c)(1),
(2) Date: Oct. 16, 2014

(87) PCT Pub. No.: WO2013/157756
PCT Pub. Date: Oct. 24, 2013

(65) Prior Publication Data
US 2015/0086942 A1    Mar. 26, 2015

(30) Foreign Application Priority Data

Apr. 19, 2012 (KR) .................. 10-2012-0041160
Mar. 27, 2013 (KR) .................. 10-2013-0032466

(51) Int. Cl.
*A61C 8/00* (2006.01)
*A61C 3/02* (2006.01)

(52) U.S. Cl.
CPC .............. *A61C 8/0024* (2013.01); *A61C 3/02* (2013.01); *A61C 8/005* (2013.01); *A61C 8/006* (2013.01);
(Continued)

(58) Field of Classification Search
CPC ....... A61C 8/0024; A61C 3/02; A61C 8/0018; A61C 8/005; A61C 8/006; A61C 8/0068;
(Continued)

(56) References Cited

U.S. PATENT DOCUMENTS

| | | | |
|---|---|---|---|
| 6,217,331 B1* | 4/2001 | Rogers ................. | A61C 8/0001 433/173 |
| 6,981,873 B2 | 1/2006 | Choi et al. .................... | 433/173 |
| 7,597,557 B2* | 10/2009 | Fromovich .......... | A61C 8/0022 433/173 |
| 2005/0043735 A1 | 2/2005 | Ahmad .......................... | 606/73 |

(Continued)

FOREIGN PATENT DOCUMENTS

| | | |
|---|---|---|
| DE | 20304367 U1 | 8/2004 |
| EP | 0214962 B1 | 6/1990 |

(Continued)

OTHER PUBLICATIONS

International Search Report (ISR) in PCT/KR2013/002621, dated Aug. 8, 2013.

*Primary Examiner* — Nicholas Lucchesi
(74) *Attorney, Agent, or Firm* — Harness, Dickey & Pierce, P.L.C.

(57) ABSTRACT

The present invention relates to a dental implant fixture for implanting a correction tooth as a dental implant into alveolar bone. Particularly, the dental implant fixture has self-vertical drilling, self-horizontal drilling, self-cutting, self-condensing, and self-direction changing functions. The dental implant fixture can increase primary stability and penetration performance, has good ability to correct implantation errors, and can minimize the need for drilling that increases the probability of error or failure.

19 Claims, 31 Drawing Sheets

(52) U.S. Cl.
CPC .......... *A61C 8/0018* (2013.01); *A61C 8/0048* (2013.01); *A61C 8/0068* (2013.01); *A61C 8/0069* (2013.01); *A61C 8/0075* (2013.01); *A61C 8/0045* (2013.01)

(58) Field of Classification Search
CPC ... A61C 8/0069; A61C 8/0075; A61C 8/0045; A61C 8/0048
USPC ........................................................ 433/174
See application file for complete search history.

(56) References Cited

U.S. PATENT DOCUMENTS

| | | | | |
|---|---|---|---|---|
| 2008/0261176 A1* | 10/2008 | Hurson | ................ | A61C 8/0022 433/174 |
| 2010/0233657 A1* | 9/2010 | Teichmann | ........ | A61B 17/1655 433/174 |
| 2011/0070557 A1* | 3/2011 | Elyav | .................... | A61C 8/0018 433/174 |
| 2011/0117522 A1* | 5/2011 | Verma | .................. | A61C 8/0022 433/174 |
| 2014/0200620 A1* | 7/2014 | Yahav | .................. | A61C 8/0022 606/315 |
| 2016/0166358 A1* | 6/2016 | Thome | ................. | A61C 8/0025 433/174 |

FOREIGN PATENT DOCUMENTS

| | | | | |
|---|---|---|---|---|
| EP | 1 457 165 B1 | 6/2011 | | |
| KR | 10-2002-0045638 | 6/2002 | ............. | A61C 13/00 |
| KR | 10-0807150 | 2/2008 | ............... | A61C 8/00 |

\* cited by examiner

Implant fixture C

Implant fixture D

TOOTH IMPLANT

CROSS-REFERENCE TO RELATED APPLICATIONS

This application is a national phase application of PCT Application No. PCT/KR2013/002621, filed on Mar. 29, 2013, which claims the benefit and priority to Korean Patent Application No. 10-2012-0041160, filed Apr. 19, 2012 and Korean Patent Application No. 10-2013-0032466, filed Mar. 27, 2013. The entire disclosures of the applications identified in this paragraph are incorporated herein by references.

TECHNICAL FIELD

The present invention relates to a dental implant fixture, and more specifically to a dental implant fixture that has a vertical self-drilling function enabling vertical penetration, achieves high primary stability, and with other related components allows immediate loading.

BACKGROUND

An implant generally refers to an artificial tooth that is obtained by inserting a screw made of titanium into alveolar bone and engaging a separate prosthetic tooth (or a correction tooth) with the inserted implant.

Recent developments in implant technology and problems of conventional implants will be discussed below.

First, a gap is inevitably formed where a prosthetic tooth (or a correction tooth) is connected to provide an environment for bacterial proliferation which may produce oral malodor together with the residual food in the gap.

Second, according to a known implantation method illustrated in FIG. 2, a bone 101 is cut with a surgical tool (or a drill) 110 to form a hole (or an aperture) 102, and an implant fixture 20 is implanted into the bone through the hole 102. Drilling itself is an operation that destroys and weakens the bone 101. However, technically drilling and making a hole are required for the implantation. Since the drill is basically different in shape from the implant fixture 20 to be implanted, it is absolutely impossible to accurately align the implant fixture 20 with the hole formed by drilling. If the hole formed by drilling is large, a dead space (or an empty space) 105 may be created lowering the primary stability, thereby increasing the possibility of implant failure. Meanwhile, if the hole is small, the pressure of the implant fixture applied to the bone increases, resulting in bone destruction. If the hole or aperture formed by drilling is short, the implant fixture may not be completely inserted into the hole. Meanwhile, if the hole or aperture is long, the dead space 105 may be formed under the implant fixture even when the implant fixture is fully inserted into the hole, and as a result, the bone cannot support the vertical force.

In the case where there is a risk that an implant fixture may be erroneously placed into a hole drilled in a false direction, a new hole must be formed by drilling. In this case, the bone may be severely destroyed, causing implant failure. It is thus believed that conventional cylindrical implant fixtures do not have any vertical drilling function, or if any, cannot perform a substantial vertical drilling function in spite of advertisements of their makers. This is because such a cylindrical implant fixture has a flat or convex tip and cutting blades thereof are distant from the center of a core, making it impossible to reduce the central portion of the alveolar bone in contact with the core. A conventional implant fixture without drilling function at the tip is not advancing smoothly when the direction of insertion is to be changed or when it is rotated with compression to place it deeper or obtain higher anchoring. In the state where moving forward is not accommodated, arbitrary rotation of the implant fixture causes complete cutting of the bone in an area where the cutting blades reach and leads to loosening of the implant fixture. Even when slight advancing is permitted, an excessive pressure is applied to an upper screw of the implant fixture where no cutting blade is provided. In the case where the implant fixture is not advanced reducing the alveolar bone but is forcibly pushed into the bone due to the excessive pressure by the rotation of the upper screw, the deeply seated implant fixture brings about bone destruction because the implant fixture is not inserted by bone resection of the tip but is pushed into the bone plate. As a result, dead spaces are formed at screw valleys which are not fully filled with the cut alveolar bone chips. In conclusion, the use of the implant fixture including the tip with no drilling function increases bone destruction. This situation is continuously worsened by bone compression at middle and upper portions of the implant fixture. In an attempt to overcome such problems, additional or frequent drilling of bone is performed leading to problems of increased bone loss and complicated surgical process, inherent with placing the conventional implants.

For reference, FIG. 1a illustrates an implant fixture of Korean Patent Application No. 10-2009-7024276 entitled "Dental implant". The prior art aims to improve a condensing effect by increasing the thickness of the implant fixture 20 from a distal end 24 to a proximal end 22 thereof, but cannot achieve drilling or cutting effect because two spiral grooves 48 extend only to a middle portion of the implant fixture in the longitudinal direction of the implant fixture. Despite the effort to improve a condensing effect, an excessive force is applied to bone in the course of insertion of implant. In particular, since the implant fixture includes a flat shelf-shaped tip, the vertical self-drilling function of the implant fixture is so little that vertical penetration is impossible. Thus, this technique fails to solve the problems of implant fixtures invented before.

The change of direction of the dental implant is not allowed because of no vertical penetration or advancing function. The implant fixture has a two-body structure as implant is connected to a supra structure of an artificial tooth. Due to this structure, a fine gap is inevitably formed between a connection screw and the implant fixture. As a result, bacteria propagate and food residue is collected in the gap to produce an unpleasant smell.

In addition to the problems of the conventional implant fixtures during placement, problems associated with immediate loading and immediate placement will be described to propose improvements of implant fixtures. Dental implant placement can be classified into immediate placement and delayed placement. According to immediate placement, an implant fixture is placed immediately after a tooth is pulled out. According to delayed placement, an implant fixture is inserted after a predetermined period of time (about two months) following tooth extraction. Dental implants can also be classified into immediate loading and delayed loading. According to immediate loading, a dental prosthesis is immediately engaged with an upper portion of an implant fixture for mastication and aesthetic functions after implantation. According to delayed loading, a dental prosthesis is engaged with an implant fixture 3 to 6 months after implantation.

The functions of immediate loading can be divided into aesthetic and actual mastication functions. Primarily anterior teeth are for the aesthetic function and posterior teeth are for the mastication function. Particularly, immediate loading is further required for an aesthetic feeling of a patient. However, most implant fixtures known in the art are based on delayed loading after delayed placement. The reason why immediate loading cannot be applied to conventional implant fixtures is not because the implant fixtures are intentionally designed for delayed loading, but because existing designs of the implant fixtures are not suitable or disadvantageous for immediate loading. For this reason, various problems occur. In the course of delayed implantation and delayed loading, it is difficult to utilize a mastication function after implantation and the aesthetic appearance of the patient' face may be damaged, restricting the social life of the patient. Immediate placement and immediate loading are considered to avoid this problem, but they are impossible to perform in view of the physiological properties of human bones and the shapes of existing implant fixtures.

To elucidate the reason, it is necessary to understand the physiological properties of human bones to some extent. Human bones can be generally classified into lamellar bones and woven bones. Lamellar bones refer to natural bones that perform normal physiological functions. Woven bones are formed, for example, when human bones are damaged or stress fractured after long-term use or when hormonal changes occur. In post-menopausal women, woven bones are formed when bones are weakened due to a reduction in estrogen level or are fractured, or when bone resorption is accelerated to reduce bone mass or make bones brittle.

When holes are drilled into lamellar bones for dental implantation, the bones are changed to woven bones. Woven bones are weaker than lamellar bones, suffer from an abnormal resorption profile, or become very weak during regeneration. When additional stimulation is applied during immediate loading, woven bones may be further destroyed rather than being regenerated or may be converted into flesh (fibrous tissue; soft tissue) instead of bones (hard tissue) through fibrous metaplasia. This is because stem cells or mesenchymal cells are converted into bone or cartilage, fibrous tissue, muscle, adipocytes, ligament, loose connective tissue or granulation tissue depending on environments and situations. That is, woven bones are differentiated into various tissues depending on whether appropriate environments are available or not.

Here, it can be proposed that immediate placement and immediate loading are possible when an implant fixture is placed to maintain lamellar bones as much as possible without being changed to woven bones during dental implantation, or an implant fixture is formed with ideal and most desirable structure to maintain lamellar ones as much as possible. For immediate loading, a bone should be held in close contact with an implant fixture and the state of the bone should also be a lamellar bone. Moreover, the lamellar bone in the horizontal direction should be secured as much as possible. As described above, conventional implant fixtures based on conventional drilling techniques may be structurally damaged by drilling for implantation. This damage changes lamellar bones to woven bones. That is, a dental implant fixture works properly when destroyed lamellar bones are changed to woven bones and are restored to lamellar bones surrounding the dental implant fixture.

A conventional cylindrical implant fixture is disadvantageous for immediate loading due to insufficient structural strength of horizontal bone resisting a vertical force. This is because a force is substantially concentrated on a tip of the cylindrical structure and a screw having a small horizontal area. Disc type dental implant fixtures are advantageous for immediate loading, but the techniques that can precisely place the dental implant fixtures are not good enough for practical application. Now, an explanation will be given concerning the implantation of a typical disc type dental implant fixture claiming to be capable of immediate loading.

In connection with immediate loading, a disc type dental implant fixture of FIG. 1b can be mentioned. Some examples of such disc type dental implant fixtures are found in EP 1 457 165 B1, DE 203 04 367 U1, and EP 0 214 962 B1. FIG. 1b illustrates the shapes of a known dental implant fixture (see FIGS. 8 and 9). The photographs of FIG. 1b show an implantation process of the dental implant fixture, which is the same or similar to a conventional implantation process for immediate loading.

Referring to the photographs of FIG. 1b, the implantation process of the disc type dental implant fixture illustrated in FIGS. 8 and 9 of FIG. 1b is explained below. The lateral sides of an alveolar bone are directly removed by cutting, and the dental implant fixture is immediately implanted and loaded therein. The cutting of the alveolar bone is shown in Photograph 1 and the insertion of the disc type dental implant fixture into the alveolar bone is shown in the other photographs. An accurate position for the implant fixture is secured and an artificial tooth is coupled to the implant fixture for immediate loading, as shown in Photograph 8.

The conventional dental implant fixture is advantageous for immediate loading due to its large horizontal sectional area. However, since implantation of the conventional dental implant fixture proceeds after the lateral sides of alveolar bone are cut, the implantation procedure is complicated and entails much bone loss. Since the alveolar bone cannot be cut precisely in the same form as the conventional dental implant fixture, numerous dead spaces are created. Further, since the dental implant fixture is larger in size than the teeth, the dental implant fixture cannot replace the individual tooth, resulting in a low success rate of implantation. Revision surgery due to this failure leads to extreme bone destruction.

As explained above, the conventional cylindrical dental implant fixtures destroy lamellar bones upon implantation due to their physical structures. Destroyed lamellar bones are changed to woven bones, which are then turned to lamellar bones. In this healing course, the bones become soft and mushy and the dental implant fixtures are not fixed to the bones, making it difficult to couple artificial teeth to the implant fixture. Thus, much time is required for bone regeneration to fix the dental implant fixtures to bones. For this reason, conventional techniques for the implantation of dental implant fixtures are limited to delayed loading. The conventional disc type dental implant fixture has the same problems as described above. Since the conventional disc type dental implant fixture must be buried in bone for delayed loading without any load for a long time, it is coupled to a prosthetic appliance, which is to be connected to a tooth. A problem associated with this structure is the formation of gaps at the connection. The gaps provide an environment for microbial proliferation. For example, microorganisms propagate in the gaps to produce an unpleasant smell and bacterial infection shortens the service life of the dental implant fixture. A rotational force (or a torque) is applied to the dental implant fixture when prosthesis is connected by a connection screw or is disconnected. This force may cause the failure of the dental implant fixture placed with low stability.

Technical Problem

The present invention is intended to provide a dental implant fixture for implanting a correction tooth as a dental implant into the alveolar bone. Particularly, the present invention is intended to provide a dental implant fixture that has a self-vertical drilling function resulting from a unique propeller shape of a tip, and an excellent self-lateral cutting function when rotationally inserting or retrieving the fixture enabled by a multi-cutting edge system with the core and screw cutting surfaces in various angles and depths.

The dental implant fixture of the present invention also has a self-reverse cutting function and a self-bone condensing function for stability (i.e. a function to densify the bone tissue and to obtain proper stability by applying pressure to the bone). The self-condensing function is achieved by applying an optimal pressure to the bone while improving the bone quality and stability due to an increase in the diameter and thickness of a screw and a stepwise, circulating, and repeated increase in the diameter of a core. These functions are enabled by a self-pressure adjusting system. The dental implant fixture of the present invention is also imparted with a self-autologous bone filling function to fill a dead space reusing the autologous human bone chips generated during bone reduction. Further, the dental implant fixture of the present invention has large distances and large depths between the screws to secure a horizontal lamellar bone as much as possible with hardly any damage to the bone.

The dental implant fixture of the present invention has maximized initial penetration and primary stability due to its unique self-vertical drilling function and can be implanted requiring no or less use of drills as a surgical instrument depending on bone quality. The dental implant fixture of the present invention can be immediately placed into a bone with inferior quality after tooth extraction, can achieve primary stability, and can be immediately connected to a tooth. Due to the self-vertical drilling function, the self-cutting function, the self-condensing function, and the self-filling function (self-autologous bone filling function), no dead space is created and the alveolar bone comes into contact with the dental implant fixture contact as much as possible, thus enabling immediate loading. The dental implant fixture of the present invention enables immediate loading for all bone quality except for the worst ones and is optimal for immediate loading. Particularly, the self-lateral cutting and self-vertical drilling functions by a multi-cutting edge system are essential for the self-insertion path changing function inherent to the dental implant fixture of the present invention, which enables a change of direction during implantation. The dental implant fixture of the present invention has a screw shape designed to deliver an external force to the bone only in the form of a vertical force (compression) that can be best withstood by the bone. A tensile force or shear force may be generated at an angle where bone destruction is caused depending on the form of the screw of the implant fixture. The dental implant fixture of the present invention is designed to deliver an implantation pressure in the form of a vertical force. In addition, the dental implant fixture of the present invention is designed to deliver a force applied by the dental implant fixture to the bone in the form of a vertical force even during function after implantation. Due to these designs, the dental implant fixture of the present invention can prevent the bone from being weakened and destroyed by a shear force and/or a horizontal force other than a vertical force. This feature is achieved by the self-force direction changing function to convert a shear force and/or a horizontal force into a vertical force.

Due to the above innovative capabilities, the dental implant fixture of the present invention can secure excellent stability for immediate placement and immediate loading and in bones with inferior quality, can increase primary stability and penetration performance, has good capability to correct implantation errors, and can minimize the need for drilling that increases the probability of error or failure.

The dental implant fixture of the present invention includes a tip section formed at the lower end thereof to perform horizontal cutting and to induce drilling, and a body section disposed at the upper end of the tip section and consisting of a drilling portion, a support portion, and a seating portion, wherein a core and screw lines are fixated in the drilled alveolar bone to achieve tight coupling to the bone, and the thicknesses of side surfaces of the drilling portion, the support portion and the seating portion are gradually increased such that the dental implant fixture can be coupled to the alveolar bone without applying an excessive force to the bone.

The dental implant fixture of the present invention enables immediate loading and immediate functioning, which have been considered impossible to achieve in the prior art. The dental implant fixture of the present invention also adopts not only a two-body type structure but also a one-body type structure to prevent side effects (such as malodor, infection, and inflammation) caused by the proliferation of microorganisms in the connecting screw of a conventional two-body type implant fixture.

Technical Solution

In accordance with one aspect of the present invention, there is provided a dental implant fixture having a downward tapered shape and formed with a screw on the outer circumferential surface thereof. Specifically, the dental implant fixture includes: a tip section 10 whose lower central portion is removed such that the alveolar bone 1 of a tooth is directly drilled from the lower end of the tip section; a body section 50 integrally formed with the upper end of the tip section 10 and having screw lines 52 spirally protruding from the outer circumferential surface of a center core 51; and a tooth connecting section 60 disposed at the upper end of a seating portion 40 extending from the body section 50.

The body section 50 is an integral body including a drilling portion 20 formed at the upper end of the tip section 10, a support portion 30 formed at the upper end of the drilling portion 20, and a seating portion 40 formed at the upper end of the support portion 30. Each of the drilling portion 20, the support portion 30 and the seating portion 40 includes the core 51 acting as a shaft and the screw lines 52 spirally protruding from the outer circumferential surface of the core 51. The tooth connecting section 60 forms a two-body type implant fixture A having spaces 85, 86 concavely recessed in the downward direction and engaged with a prosthetic tooth. Alternatively, the tooth connecting section 60 may form a one-body type implant fixture B having a tooth engaging section 85A straightly extending upward from the upper portion of the tooth connecting section. Each of the one-body type implant fixture B and the two-body type implant fixture A is formed with sealing lines 61 circumferentially protruding from the cylindrical outer circumferential surface of the tooth connecting section 60.

The screw lines 52 of the body section 50 are of a single line type in which one spiral screw line 52 protruding from the outer circumferential surface of the center core 51 is spirally rotated. Alternatively, the screw lines 52 are of a multiple line type in which a plurality of spiral screw lines 52 protruding from the outer circumferential surface of the center core 51 is spirally rotated. The core 51 of the one-body type implant fixture B is formed proximate to a center-line CL of the one-body type implant fixture B and has a thickness of 1.0 mm to 3.0 mm, and the screw lines have pitches ranging from 3.0 mm to 5.0 mm. The core 51 of a one-body type implant fixture C is formed as a line proximate to a center-line CL of the one-body type implant fixture C and having a thickness of 0.01 mm to 1.0 mm, and the screw lines 52 have pitches ranging from 4.2 mm to 5.0 mm.

The body section 50 includes the screw lines 52 and valleys 53. The screw lines 52 have side surfaces 55 whose thicknesses gradually increase in the order of the drilling portion 20, the support portion 30 and the seating portion 40. The thicknesses of the side surfaces 55 of the screw lines 52 increase gradually in the upward direction in each of the drilling portion 20, the support portion 30 and the seating portion 40. The body section 50 includes screw lines 52 and valleys 53. Each of the screw lines 52 has a cross-section that forms a side surface 55 including a tapered upper end surface 56 and a tapered lower end surface 57. The tapered upper end surface 56 forms a larger angle with respect to the horizontal plane than the tapered lower end surface 57.

Valleys 53 of the core 51 of the body section 50 are tapered downward such that upper end cores 51-1 have a larger diameter than lower end cores 51-2. Assuming that the core 51 consists of two upper and lower cores 51 divided by the screw line 52 in the vertical direction, the upper core 51 is tapered such that a first upper end core 51-1 and a first lower end core 51-2 have different diameters L1, L2, respectively, and the lower core 51 is also tapered such that a second upper end core 51-1 and a second lower end core 51-2 have different diameters L3, L4, respectively. The diameters increase in the order of L4<L2<L3<L1. The body section 50 has any of one to four rows of guide grooves 70 spirally ascending vertically along the outer circumferential surface thereof.

The screw lines 52 formed at the right sides of the guide grooves 70 are cut to form cutter portions 71. Each of the cutter portions 71 is tapered downward to the right side by cutting the screw line 52 downward to the right side. The screw lines 52 formed at the left sides of the guide grooves 70 are cut upward to the left side to form counterpart cutter portions 72.

The cutter portions 71 or the counterpart cutter portions 72 are formed in the drilling portion 20 and the support portion 30. The cutter portions 71 or the counterpart cutter portions 72 are formed in one or two rows of guide grooves 90. The tip section 10 is manufactured in the form of a propeller for horizontal cutting of the alveolar bone 1 by removing portions of the core underlying a first screw line.

The lower center core 51 of the tip section 10 has a recess 13 for additional cutting. The recess 13 is formed at the center of the bottom surface of the tip section 10. The recess 13 may have various shapes, for example, circular (a), polygonal, thunderbolt-like, and star-like (e) shapes. The tip section 10 may have one to four cutting tips 11.

Each of the cutting tips 11 has a tip cutter portion 12, which is formed by tapering the upper end of the cutting tip 11 in the clockwise direction.

In accordance with a further aspect of the present invention, there is provided a dental implant fixture having a downward tapered shape and formed with a screw on the outer circumferential surface thereof. Specifically, the dental implant fixture includes: a tip section 10 at the bottom for directly drilling the alveolar bone 1 of a tooth; a body section 110 including a core 102 integrally formed with the upper end of the tip section 10 and acting as a central shaft, and one row of screw lines 103 spirally formed along the outer circumferential surface of the core 102 such that the alveolar bone 1 is cut and drilled through screw rotation; a connection section 60 ascending from the upper end of the body section 110 to have a circular outer circumferential surface; and a tooth engaging section 85A extending from the upper end of the connection section 60 to be directly connected to a tooth. The tip section 10 is formed such that a portion of the core 102 at a distal end of the tip section 10 is removed and the distal ends of the one row of spiral screw lines 103 are located concentrically at predetermined distances from the center-line.

In accordance with another aspect of the present invention, there is provided a one-body type dental implant fixture having a screw formed around the outer circumferential surface thereof. Specifically, the dental implant fixture includes: a tip section 10 at the bottom for directly drilling the alveolar bone 1 of a tooth; a body section 50 including a drilling portion 20 formed at the upper end of the tip section 10, a support portion 30 formed at the upper end of the drilling portion 20, and a seating portion 40 formed at the upper end of the support portion 30, these portions being formed integrally and each thereof including a core 51 acting as a shaft and screw lines 52 spirally protruding from the outer circumferential surface of the core 51; a connection section 60 formed at the upper end of the seating portion 40 to have a vertical cylindrical shape; and a tooth engaging section 85A extending from the upper end of the connection section 60 and engaged with the tooth.

In accordance with yet another aspect of the present invention, there is provided a one-body type dental implant fixture having a screw formed around the outer circumferential surface thereof. Specifically, the dental implant fixture includes: a tip section 10 at the bottom for directly drilling the alveolar bone 1 of a tooth; a body section 50 including a drilling portion 20 formed at the upper end of the tip section 10, a support portion 30 formed at the upper end of the drilling portion 20, and a seating portion 40 formed at the upper end of the support portion 30, these portions being formed integrally and each thereof including a core 51 acting as a shaft and screw lines 52 spirally protruding from the outer circumferential surface of the core 51; a connection section 60 formed at the upper end of the seating portion 40 to have a vertical cylindrical shape; and a tooth engaging section 85A extending from the upper end of the connection section 60 and engaged with the tooth, wherein the core 51 of the one-body type implant fixture C is formed as a line proximate to a center-line CL of the implant fixture C and having a thickness of 0.01 mm to 1.0 mm when the screw lines 52 are formed.

Advantageous Effects

As the dental implant fixture of the present invention rotates about a center axis, it is inserted into a bone tissue composed of a cortical bone and a calculus bone to form an artificial tooth root. The dental implant fixture facilitates dental surgery due to its drilling function.

The dental implant fixture of the present invention is designed such that the outer diameter of the body section implanted into a calculus bone increases upward. Due to this design, the dental implant fixture pressurizes bone tissue around the calculus bone to secure primary stability and can optimally distribute a load to prevent the occurrence of bone reabsorption after implantation.

The cutting portions formed in the screw lines or the tip section at the lowermost end of the implant fixture has a drilling function. Due to this drilling function, a dentist can change the implantation direction of the implant fixture to a desired direction and can implant the implant fixture even when an initial hole is wrongly formed by a drill or a hole is made by the implant fixture later.

The implant fixture of the present invention enables immediate placement and immediate loading, resulting in improvements in mastication function and aesthetic feeling immediately after implantation.

The implant fixture of the present invention is structured to protect horizontal bones. This structure enables immediate loading. The implant fixture has a one-body structure free from gaps. This structure can prevent the proliferation of bacteria and the production of malodor.

SUMMARY

The present invention provides an implant fixture for dental surgery. Hereinafter, constitutions and effects of the present invention will be described with reference to FIGS. 3 to 19.

The background of Korean Patent Application No. 10-2012-0041160 (filed on Apr. 19, 2012) entitled "Dental implant", which was filed by the present applicant, and the purposes of development of the new implant fixtures have already been explained in the background art. The present invention adds three main embodiments to the prior application of the present applicant. FIG. 4a illustrates a total of four embodiments of the present invention. FIG. 4b illustrates five embodiments including one which needs to be distinguished. In FIG. 4a, (a) illustrates a two-body type implant fixture of the prior application, and (b) illustrates a one-body type implant fixture. That is, (b) of FIG. 4 illustrates an embodiment in which a body section of the two-body type implant fixture illustrated in (a) is applied to a one-body type implant fixture. Since the two-body type implant fixture is necessarily required to have an inner hole for connection at the upper portion thereof, it is difficult to manufacture into a one-body type. The present invention provides a one-body type implant fixture in which the pitch and depth of a screw increase to make a core significantly smaller and thinner than the core of the two-body type implant fixture while maintaining the outer shape of a cylindrical connection section.

(c) of FIG. 4a illustrates a one-body type implant fixture in which a central core is further removed to have a smaller thickness than the core of the implant fixture of (b) and the cylindrical connection section is replaced by continuous screw lines 55. The core 51 of the implant fixture is formed as a line proximate to a center-line CL and having a thickness of 0.01 mm to 0.5 mm when the screw lines are formed. (d) of FIG. 4a illustrates a one-body type implant fixture in which a portion of a core at a distal end of a tip section is removed and a single screw line protrudes concentrically with the center of the core and is spaced a predetermined distance from the center of the core.

FIG. 4b illustrates implant fixtures A and A', which are embodiments subdivided from the implant fixture A illustrated in FIG. 4a. A difference between both implant fixtures resides in a tip section. Specifically, the implant fixture A includes a tip section 10 having a concave recess 13 and the implant fixture A' includes a propeller type tip section. Although the implant fixture A, the implant fixture A', and other implant fixtures B, C, and D are distinguished from each other in FIGS. 4a and 4b, these implant fixtures are preferred embodiments of the present invention. Thus, the present invention will be described based on FIG. 4b.

It should be noted that each of the embodiments illustrated in (a) of FIG. 4a and (a) of FIG. 4b is referred to the implant fixture A, the embodiment illustrated in (b) of FIG. 4b is referred to as the implant fixture A', each of the embodiments illustrated in (b) of FIG. 4a and (c) of FIG. 4b is referred to as the implant fixture B, each of the embodiments illustrated in (c) of FIG. 4a and (d) of FIG. 4a is referred to as the implant fixture C, and each of the embodiments illustrated in (d) of FIG. 4a and (e) of FIG. 4b is referred to as the implant fixture D.

As illustrated, the dental implant fixture of the present invention has a downward tapered shape and is formed with a screw on the outer circumferential surface thereof. Specifically, the dental implant fixture includes: a propeller type tip section 10 whose lower central portion is removed such that the alveolar bone 1 of a tooth can be directly drilled from the lower end of the tip section; a body section 50 integrally formed with the upper end of the tip section 10 and having screw lines 52 spirally protruding from the outer circumferential surface of a center core 51; and a tooth connecting section 60 disposed at the upper end of a seating portion 40 extending from the body section 50.

That is, the dental implant fixture of the present invention is characterized in that the center of the bottom surface of the tip section 10 is removed. FIG. 4c illustrates tip sections of the implant fixtures according to the embodiments of the present invention. Although the six embodiments of FIG. 4c illustrate only the tip sections 10 formed at the distal ends of the implant fixtures, it should be noted that the center of the bottom surface of each tip section 10 may have a concave recess, a propeller shape, and other structural space shapes. In more detail, portions of the core underlying a first screw line are removed to form a propeller shape in which only screw threads remain on the tip section, or the central portion of the core is substantially removed to form a concave recess 13.

In each of the embodiment illustrated in (a) of FIG. 4b and (a) of FIG. 4c, the tip section 10 has a concave recess 13, which will be described below. In each of the embodiments illustrated in (b) of FIG. 4b and (b) of FIG. 4c, the tip section 10 has a propeller shape. In each of the embodiments illustrated in (c) of FIG. 4b and (c) of FIG. 4c, the core 51 is removed deeper. In each of the embodiments illustrated in (d) of FIG. 4b and (d) of FIG. 4c, the core is removed deeper than the core illustrated in (c) of FIG. 4c. In these embodiments, the core is removed from the lower central portion of the tip section and a concave recess or space is formed such that the core disappears substantially and only a portion thereof remains as a line. In contrast, in each of the embodiments illustrated in (d) of FIG. 4a, (c) of FIG. 4b and (e) of FIG. 4c, the core 102 is completely removed from the distal tip section 10, and a screw line 103 starts from a location spaced a certain distance from the center and is spirally wound upward on the outer circumferential surface of the core 102. Thus, these embodiments are substantially the same as or similar to the previous embodiments in that the central portion of the bottom surface of the tip section 10 remains in the form of a space, that is, the central portion of the core is removed. As a result, each of the implant fixtures A, A', B, C, and D of FIGS. 4b and 4c has a recess or a structural space at the central portion of the bottom surface of the tip section 10. The recess or structural space is easily utilized when the implant fixture is used to resect the alveolar bone 1 by rotation. The implant fixtures 100 according to the five embodiments of the present invention have the same feature that the central portion of the bottom surface of the tip section is removed and the concave recess 13 or the space remains therein. More detailed constructions of the implant fixtures will be described below.

The present invention is advantageous in that a self-drilling function can be realized through the tip section 10 formed at the lowermost end of the implant fixture. Since the tip section 10 is manufactured in the form of a propeller for vertical cutting and horizontal cutting of the alveolar bone 1, the alveolar bone 1 in face-to-face contact with the tip section 10 can be cut into slices as the tip section 10 rotates. That is, frequent rotation of the tip section 10 enables cutting of the alveolar bone 1 in face-to-face contact with the tip section into slices to induce drilling. Since a conventional implant fixture has a drilling function at the lateral side of a tip section instead of the lower side of the tip section, its drilling function substantially corresponds to side drilling by which the bone is destroyed at the side surface of the tip section, instead of vertical downward drilling. Moreover, after such a conventional implant fixture 100 penetrates the bone to a predetermined depth, it continuously idles without any further advance. This is because the tip section 10 has no ability to resect the bone in the vertical direction due to its flat shape. In contrast, the tip section 10 of the implant fixture according to the present invention maintains a state in which the tip core is removed, and thus the surface of the alveolar bone 1 in contact with the tip section 10 is cut into slices. The tip section 10 cuts the bone into thin and small chips. That is, the tip section 10 performs a drilling function to sharply cut the bone while moving forward. The connecting section 60 of the implant fixture according to the present invention has a vertical cylindrical structure.

DRAWINGS

FIG. 4b illustrates implant fixtures according to five embodiments of the present invention, including an implant fixture A' as a modification of the implant fixture A illustrated in FIG. 4a;

DETAILED DESCRIPTION

Figure 1A:
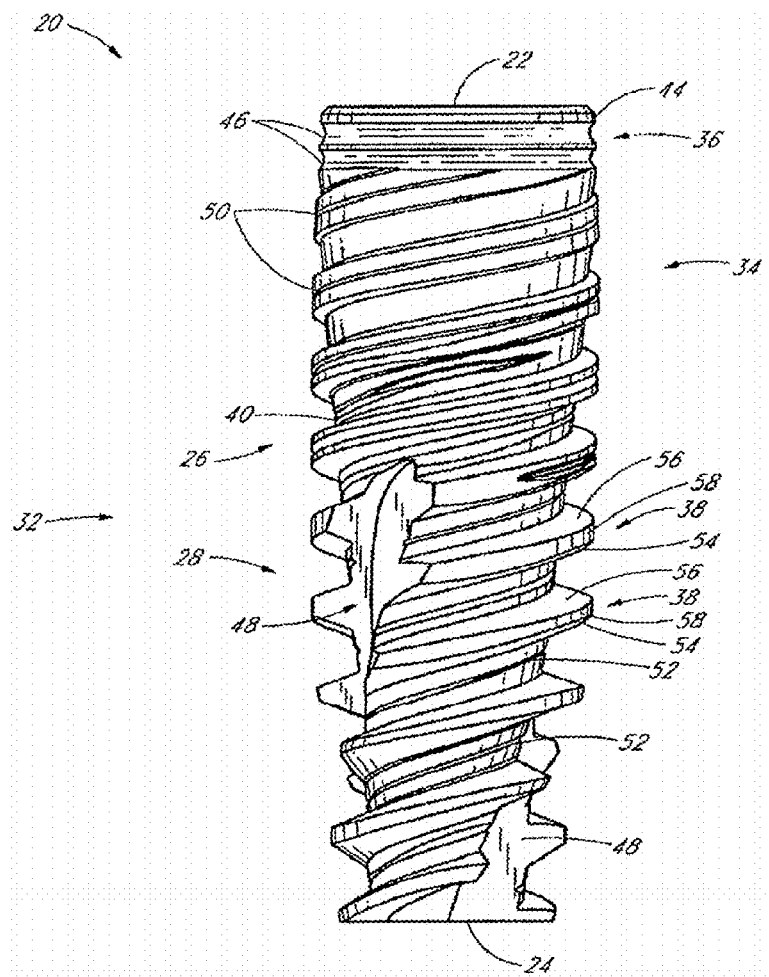
FIG. 1a illustrates a conventional implant fixture disclosed in Korean Patent Application No. 10-2009-7024276.
Figure 1B:
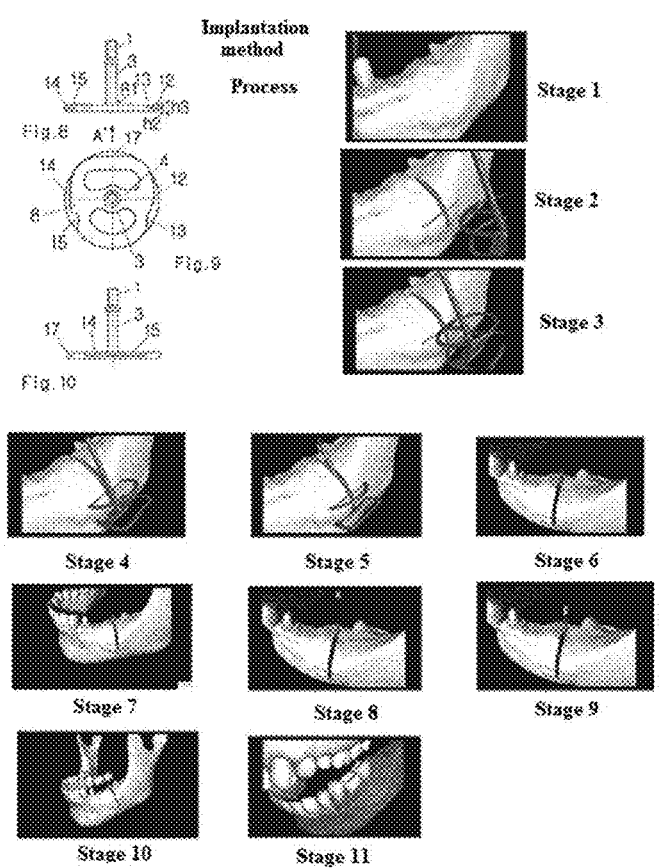
FIG. 1b illustrates a conventional disc type implant fixture and an implantation process thereof.
Figure 2:
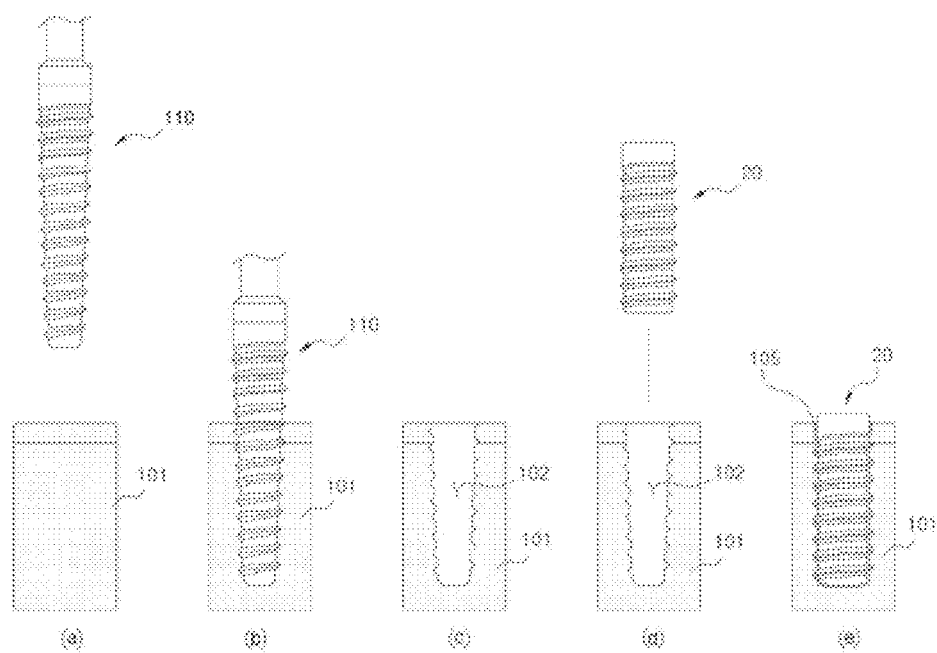
FIG. 2 illustrates the steps of implanting most of the conventional implant fixtures.
Figure 3:
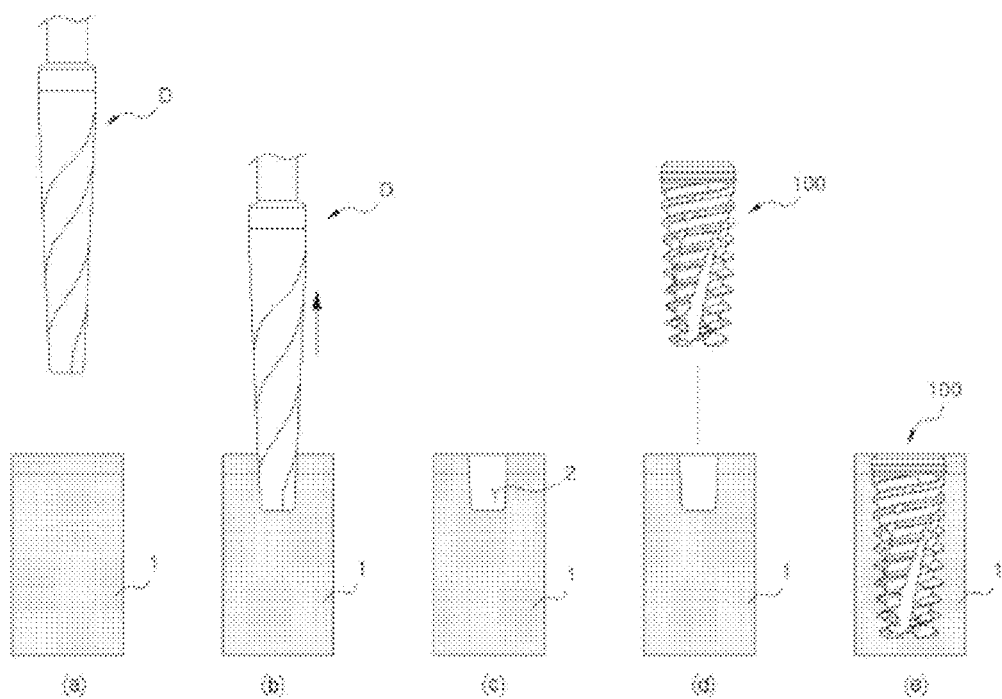
FIG. 3 illustrates the steps of implanting an implant fixture of the present invention.

Hereinafter, the present invention will be described in more detail. The implant fixture of the present invention includes a body section 50, which includes a drilling portion 20 formed at the upper end of the tip section 10, a support portion 30 formed at the upper end of the drilling portion 20, and a seating portion 40 formed at the upper end of the support portion 30. The drilling portion 20, the support portion 30, and the seating portion 40 are integrally formed with each other, and each thereof includes a core 51 acting as a shaft and screw lines 52 spirally protruding from the outer circumferential surface of the core 51.

That is, in this embodiment, only the body section 50 is explained in detail. The illustrated implant fixtures A, A' and B correspond to this embodiment. The implant fixture 100 of the present invention has a downward tapered shape, and includes a connection section 60 formed at the uppermost end thereof to have spaces 85, 86 where a prosthetic tooth can be engaged, and the body section 50 formed at the lower end of the connection section 60. The seating portion 40, the support portion 30 and the drilling portion 20 of the body section 50 are sequentially formed in this order from the top. The screw lines 52 protrude from the outer circumferential surface of the body section 50. The screw lines 52 are spirally formed along the outer circumferential surface of the body section 50. Due to this structure, valleys 53 are naturally formed between the screw lines 52. More specifically, the connection section 60, the body section 50, and the tip section 10 of the implant fixture 100 according to the present invention are sequentially formed in this order from the top, and the central portion of the implant fixture 100 corresponds to the core 51 and the screw lines 52 are formed on the outer circumference of the core 51 when viewed in the horizontal direction.

The implant fixture 100 of the present invention may have various shapes. (a) and (b) of FIG. 4b illustrate two-body type implant fixtures 100, and (c), (d), and (e) of FIG. 4b illustrate one-body type implant fixtures 100,B. In the present invention, the one-body type implant fixtures are distinguished by reference symbol B. In forming the tooth connecting section 60, the two-body type implant fixture 100 may have downwardly recessed spaces 85, 86 where a prosthetic tooth can be engaged, or the one-body type implant fixture 100,B may have a tooth engaging section 85A ascending vertically from the tooth connecting section 60.

The two-body type implant fixture 100 has a space at the upper end of the tooth connecting section 60. A screw is formed in the space and a prosthetic tooth (or an artificial tooth) can be screw-coupled to the space. In the one-body type implant fixture 100,B, a prosthetic tooth is fitted into the tooth engaging section 85A extending upward from the tooth connecting section 60. In the embodiments illustrated in FIG. 4b, the two-body type implant fixtures correspond to the implant fixture A and the implant fixture A', which is the same as the implant fixture A except for the shape of the tip section. The one-body type implant fixtures correspond to the implant fixtures B, C, and D.

The connection section 60 has sealing lines 61 circumferentially protruding from the cylindrical outer circumferential surface thereof. This structure can be seen in the implant fixtures A, A' and B of FIG. 4b. Although not illustrated, this structure may also be applied to the implant fixtures C and D. The connection section 60 is a portion into which a drill is fitted when the implant fixture 100 is implanted. The connection section 60 is also a portion into which a prosthetic tooth (or an artificial tooth) will be fitted later. Thus, this structure plays a very important role in the success rate and long-term stability of the implant fixture 100.

In the connection section 60, the largest force is applied to bone. Accordingly, it is preferred to design the connection section 60 such that a force is delivered in a direction in which the bone can well withstand the force or the magnitude of the delivered force is reduced. Since a connection section of a conventional implant fixture has a triangular dish-head shape or a tapered head shape, a force may be applied in the horizontal direction and bone may be destroyed by an excessive pressure during implantation.

In an attempt to solve the aforementioned problems, the present invention adopts a linear cylindrical shape of the connection section. In addition, the cylindrical connection section 60 is formed with sealing lines 61 protruding from the outer circumferential surface thereof. The sealing lines 61 may be arranged in plural rows for hermetic sealing. The implant fixture 100 of the present invention also has a drilling function during implantation. A recess having a predetermined depth is formed in the alveolar bone 1, and the implant fixture 100 is brought into face-to-face contact with the bone and is rotated in the recess using a screwdriver. As a result, the distal tip section 10 penetrates and drills the alveolar bone 1. At this time, the alveolar bone 1 is cut into slices, and the slices remain in the hole 2 between the outer circumferential surface of the implant fixture 100 and the alveolar bone 1, and are moved to the upper end of the hole 2 by rotation of the implant fixture 100. The slices are discharged to the outside through guide grooves 70 to minimize implantation resistance in the initial stage of implantation. In the late stage of implantation, however, the sealing lines 61 block the alveolar bone chips from being discharged to the outside. When the implant fixture 100 is further rotated for implantation, the autologous bone chips cannot escape from the guide grooves 70 and other dead spaces, and are then filling the dead spaces.

That is, the alveolar bone 1 is discharged to the outside in the initial stage, but the sliced alveolar bone 1 and the chipped alveolar bone 1 are accumulated in the first part of the hole 2 which is sealed off by the sealing lines 61 of the connection section 60 as the implant fixture 100 is being inserted to a certain degree. The sliced alveolar bone 1 is prevented from being wasted by being discharged outside on the basis of the principle that the sliced alveolar bone 1 is easily converted and regenerated into a new bone or cartilage in the oral cavity of a patient. The sealing lines 61 serve to further improve the durability of the connection section 60. In the case where a load is applied while a patient eats, the conventional implant fixture 100 having grooves or the conventional implant fixture 100 including the connection section 60 with a small diameter may be torn by accumulated fatigue arising from the mastication pressure. In contrast, the connection section 60 and the sealing structure serve to reinforce the implant fixture of the present invention.

Referring again to the drawings, (a), (b) and (c) of FIG. 4b corresponds to the embodiments in which the sealing lines 61 are formed, and (d) and (e) of FIG. 4b correspond to the embodiments in which no sealing lines are formed. According to the present invention, the sealing lines 61 may be omitted from the one-body type implant fixture 100 depending on what shape the implant fixture has and where the implant fixture is used. When it is intended to insert and firmly implant the implant fixture into the alveolar bone 1, the implant fixture C having the sealing lines 61 is used for implantation. Otherwise, the implant fixtures D and E free from the sealing lines 61 are used for implantation.

Various forms of screw lines 52 may be used in other embodiments of the present invention. Specifically, each of the implant fixtures A, B and C illustrated in (a), (b) and (c) of FIG. 4a has two rows of screw lines 52, and the implant fixture D illustrated in (d) of FIG. 4a has one row of screw lines 103. Preferably, the body section 50 has a single screw line 52 that protrudes from the outer circumferential surface of the center core 51 and spirally rotates. Alternatively, the body section 50 may have a plurality of screw lines 52 that protrude from the outer circumferential surface of the center core 51 and spirally rotate.

The implant fixture 100 having two rows of screw lines 52 has better resection performance than the implant fixture 100 having one row of screw lines 103. Accordingly, the implant fixture 100 having two rows of screw lines 52 can be inserted deep into the alveolar bone 1 even at a smaller number of rotations. However, the implant fixture 100 (for example, the implant fixture D) having one row of screw lines 52 may be necessary when it is intended to place the implant fixture 100 into hard bone or narrow bone. As such, the present invention includes all such embodiments. Referring back to the drawings, the implant fixtures A, A', B, and C of FIG. 4b have two rows of screw lines 52, and the implant fixture D has one row of screw lines 52. The implant fixture of the present invention may selectively have two to four rows of screw lines 52. One or more rows of screw lines 52 may be formed depending on the characteristics of the implant fixture.

In another preferred embodiment of the present invention, the core 51 of the one-body type implant fixture 100,B may be formed proximate to a center-line CL of the one-body type implant fixture B so as to have a thickness of 1.0 mm to 3.0 mm and to form the screw lines whose pitches range from 3.0 mm to 5.0 mm. Alternatively, the core 51 of the one-body type implant fixture C may be formed as a line proximate to a center-line CL of the one-body type implant fixture C so as to have a thickness of 0.01 mm to 1.0 mm and to form the screw lines 52 whose pitches range from 4.2 mm to 5.0 mm.

That is, the embodiment in which the core 51 of the one-body type implant fixture 100,B is formed proximate to the center-line CL of the one-body type implant fixture B so as to have a thickness of 1.0 mm to 3.0 mm and to form the screw lines whose pitches range from 3.0 mm to 5.0 mm, corresponds to the implant fixture B of FIG. 4b, and the embodiment in which the core 51 of the one-body type implant fixture C is formed as a line proximate to a center-line CL of the one-body type implant fixture C so as to have a thickness of 0.01 mm to 1.0 mm and to form the screw lines 52 whose pitches range from 4.2 mm to 5.0 mm, corresponds to the implant fixture C.

Figure 4A:
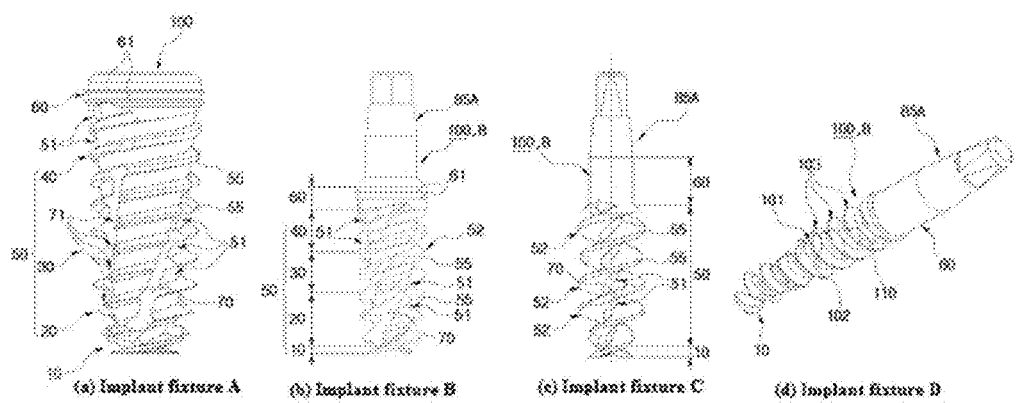
FIG. 4a illustrates implant fixtures according to four embodiments of the present invention.
Figure 4B:
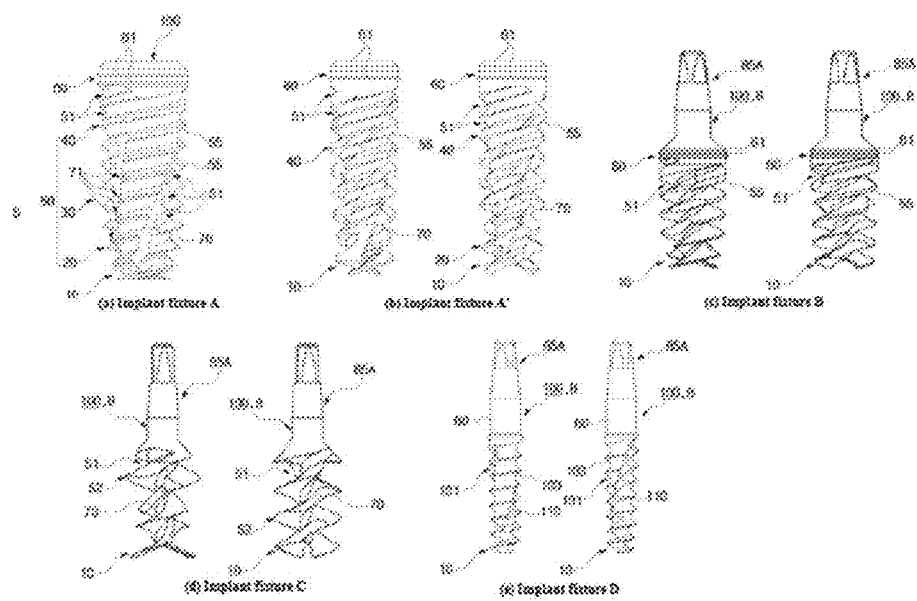

As in the embodiments illustrated in (b) of FIG. 4a, (c) of FIG. 4b, FIG. 13c, FIG. 14c, FIG. 16b, and FIG. 16c, the core of the implant fixture B has a predetermined thickness although it has a greatly reduced diameter as compared to the core of the two-body type implant fixture. Meanwhile, as illustrated in (c) of FIG. 4a, (d) of FIG. 4b, FIG. 13d, FIG. 14d, and FIG. 16d, the core of the implant fixture C is very thin. That is, in the one-body type implant fixture 100,B, the body section 50 is formed at the upper end of the tip section 10 and the screw lines 52 are formed along the outer circumferential surface of the body section 50. The seating portion 40 and the tooth connecting section 60 are formed at the upper end of the body section 50. It is, of course, common that the core 51 is formed at an inner central portion of the body section 50 and the screw lines 52 are formed at the outer surface of the core 51.

Figure 19:
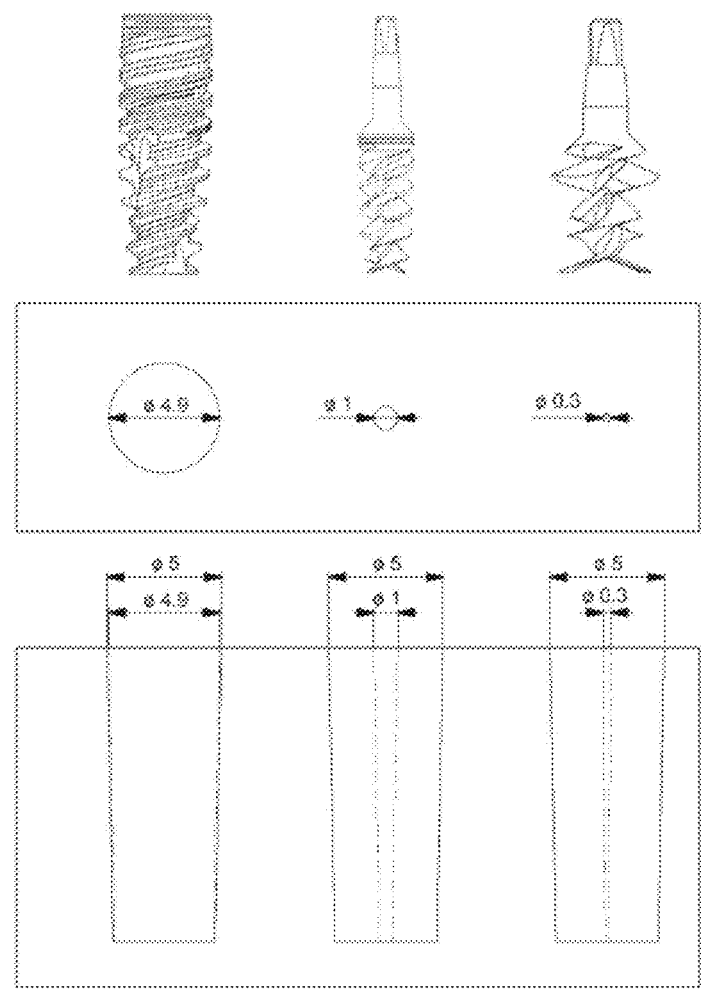
FIG. 19 illustrates modes of dental surgeries using a cylindrical implant fixture of the prior art and implant fixtures B and C according to embodiments of the present invention.

However, the core 51 of the body section 50 of the implant fixture C may be small in diameter as a whole, as in the embodiments illustrated in (c) of FIG. 4a and (d) of FIG. 4b. In this case, the implant fixture can destroy only a small portion of lamellar bone and can thus be applied to both immediate placement and immediate loading, because a small hole penetrates the lamellar bone, as illustrated in FIG. 19.

A general cylindrical implant penetrates the alveolar bone by drilling and is then implanted therein. In the course of the implantation, however, severe bone destruction occurs. FIG. 19 illustrates the degrees of bone destruction upon implantation of a conventional cylindrical implant fixture and the implant fixtures B and C of the present invention. As can be seen from FIG. 19, the conventional cylindrical implant forms a hole ab having a large diameter in the alveolar bone. In contrast, the implant fixture B forms a hole ac having a diameter of about 1 mm in the alveolar bone upon implantation. Since the diameter of the screw lines 52 of the implant fixture B is much greater than that of the core 51, the hole is enlarged to a diameter of about 5 mm, which is larger than the diameter (1 mm) of the core 51. The screw lines 52 generate a strong implantation force while reducing the degree of bone destruction. As illustrated in FIG. 19, the core 51 of the implant fixture C is extremely small in thickness and remains only as a line. Due to this structure, a hole ad having a diameter of about 0.3 mm is formed in the alveolar bone after implantation. Since the diameter of the screw lines 52 of the implant fixture C is much greater than that of the core 51, the hole is enlarged to a diameter of about 5 mm, which is larger than the diameter (0.3 mm) of the core 51. The screw lines 52 generate a strong implantation force while reducing the degree of bone destruction.

As illustrated, this is because the screw lines 52 penetrate the alveolar bone 1 while minimizing the destruction of lamellar bone.

Since the healing and regeneration process of destroyed bone is time-consuming, conventional implantation techniques are limited to delayed loading. In contrast, the implant fixture of the present invention is designed to deliver a vertical force to bone by enlarging the screw in view of the tendency of bone to withstand the vertical force. Each of the implant fixtures B, C and D penetrates only as much as necessary into the structurally sound lamellar bone in the initial stage of implantation and a space between the screw lines is filled with lamellar bone. Thus, immediate loading is possible with the implant fixtures. In particular, since the implant fixture C effective for immediate loading penetrates the structurally sound lamellar bone in the initial stage of implantation while cutting only necessary portions of the lamellar bone and the space between the screw lines 52 is filled with the lamellar bone, the implant fixture C is suitable for immediate loading.

In a conventional implant fixture having two rows of screw lines, the pitches between the screw lines are very small. That is, the conventional implant fixture is designed to have small pitches between the screw lines 52, based on the belief that the screw lines penetrating into the alveolar bone 1 must come into face-to-face contact with the alveolar bone 1 over a large surface area in order to implant the implant fixture 100 more firmly. This structure makes it difficult to maintain lamellar bone. Osteocytes are joined to each other (gap junction) to form lamellar bones while keeping their vital functions. The osteocytes are killed and the bones are destroyed if the ambient osteocytes or blood vessels are destroyed. The destroyed lamellar bones are regenerated into woven bones, which are then weakened. In contrast, large pitches between the screw lines 52 decrease the possibility of bone destruction into woven bones and allow for the preservation of lamellar bones.

Figure 16A:
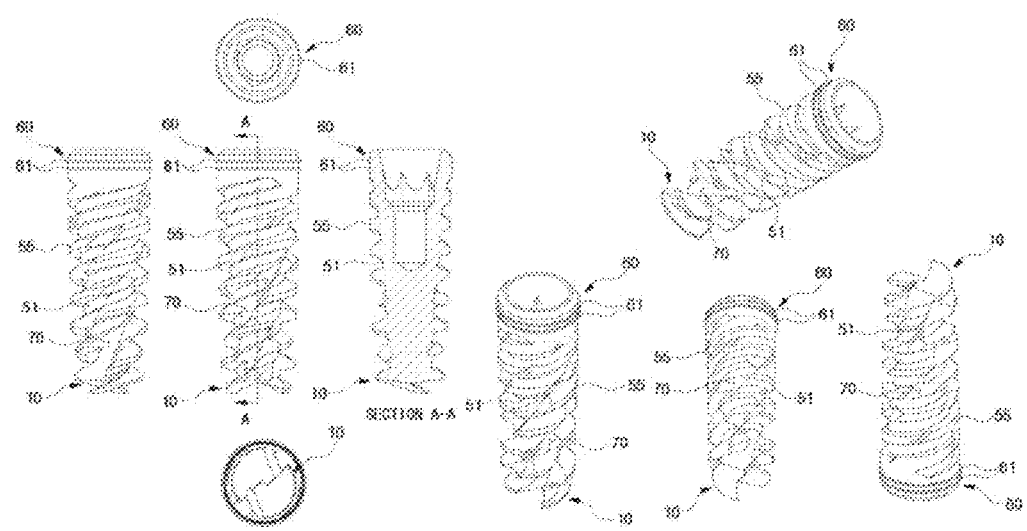
FIG. 16a illustrates an implant fixture A' of the present invention when viewed from various angles.
Figure 16B:
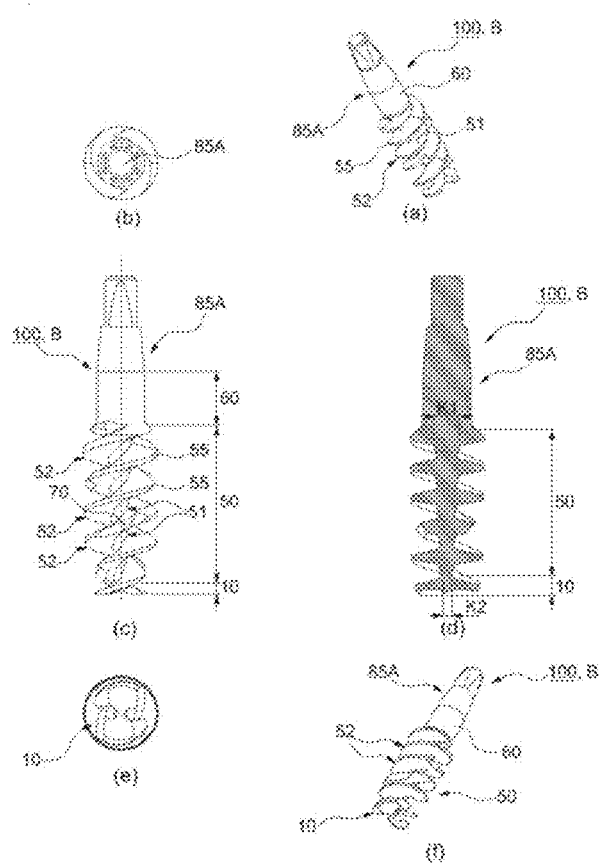
FIG. 16b illustrates an implant fixture B of the present invention when viewed from various angles.
Figure 16C:
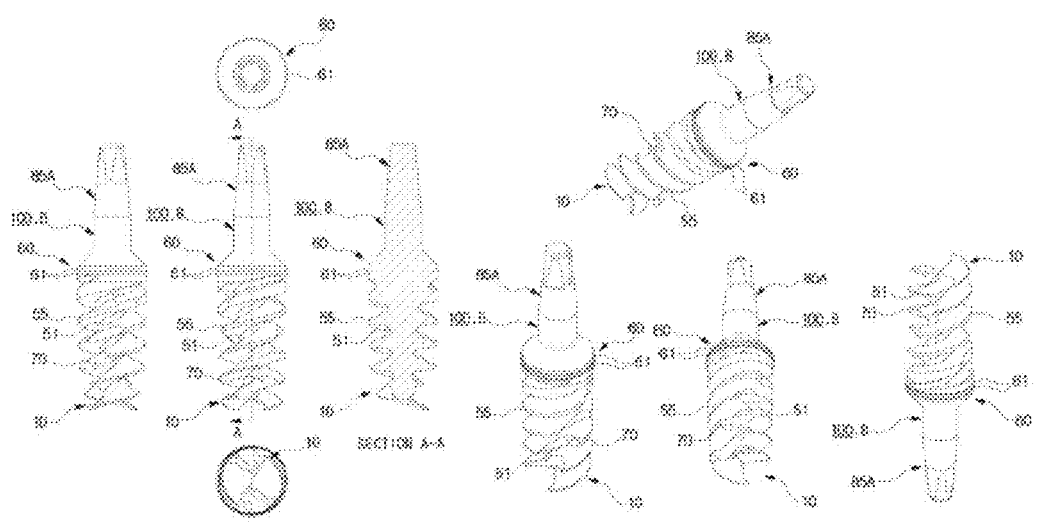
FIG. 16c illustrates an implant fixture B of the present invention that is different from the implant fixture B of FIG. 16b, when viewed from various angles.
Figure 16D:
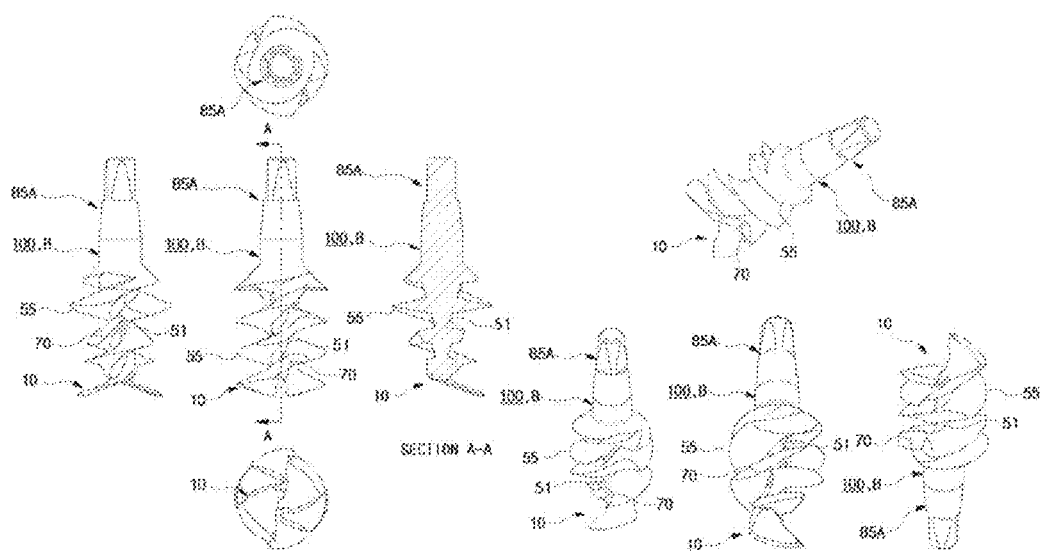
FIG. 16d illustrates an implant fixture C of the present invention when viewed from various angles.
Figure 16E:
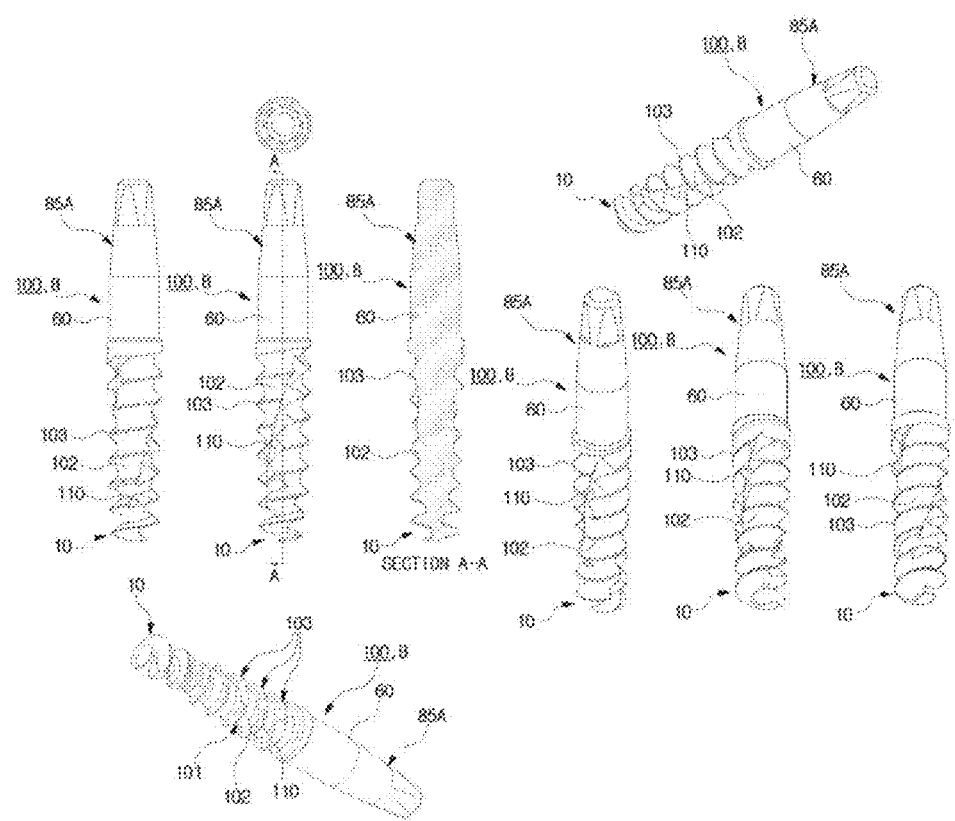
FIG. 16e illustrates an implant fixture E of the present invention when viewed from various angles.
Figure 17:
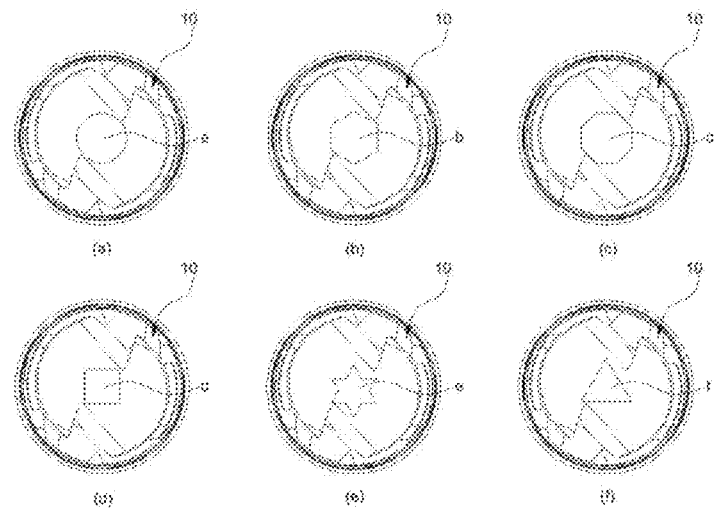
FIG. 17 illustrates tip sections usable in an implant fixture of the present invention when viewed from the bottom.
Figure 18:
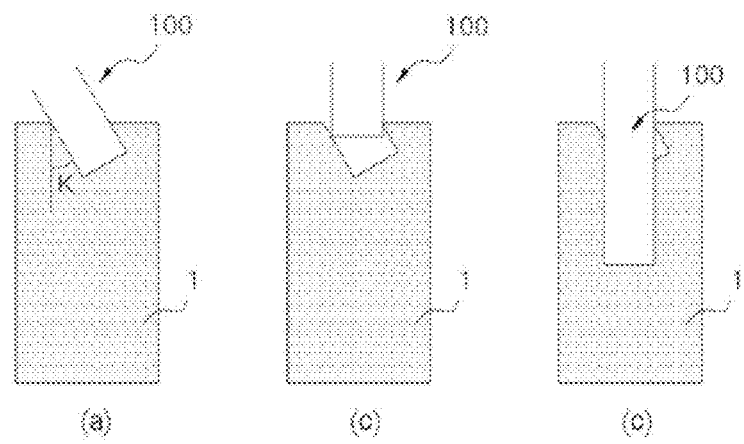
FIG. 18 illustrates a state in which an implantation error is corrected using an implant fixture of the present invention.

Consequently, each of the implant fixtures A, A', B, C, and D according to the embodiments of the present invention is constructed to have larger pitches between the screw lines than the conventional implant fixture. Due to this construction, lamellar bones can be preserved. In particular, such effects are further enhanced in the implant fixture C because the core 51 of the implant fixture C is partially removed so as to remain as a line having a small thickness. Since a substantial portion of the core of the one-body type implant fixture C is removed so as to remain as a line when compared to the implant fixtures A and B, the one-body type implant fixture C can efficiently resist a horizontal force. In the implant fixture B illustrated in FIG. 16b, the thickness K1 of the core at the uppermost portion of the body section 50 is greater than the thickness K2 of the core 51 at the lowermost portion thereof. The thickness of the core 51 ranges from 0.1 mm to 3.0 mm, which is much smaller than the thickness of the core 51 used in the conventional implant fixture 100. FIG. 16c illustrates other modifications similar to the implant fixture B illustrated in FIG. 16b. In comparison with the core of the implant fixture B, the core 51 of the implant fixture C illustrated in (d) of FIG. 4b and FIG. 16d is further removed so as to remain only as a line having an extremely small thickness. As described above, the implant fixture C is also preferred in which a substantial portion of the core 51 is removed and the core 51 has an extremely small thickness of 0.01 mm to 1.0 mm.

As the thickness of the core 51 decreases, the depth of the valleys forming the screw lines 52 increases naturally. As a result, when the implant fixture penetrates into alveolar bone, a vertical hole having a small diameter is formed in the alveolar bone and the screw lines 52 penetrate the alveolar bone over a large area in the horizontal direction to generate a firm coupling force. As illustrated in FIG. 19, the tip section 10 cuts the alveolar bone 1 into slices to form a hole having a substantially small diameter in the alveolar bone 1. The small hole minimizes damage to the lamellar bone. As such, a small amount of the alveolar bone is converted into woven bone and the lamellar bone is maintained firm, thus enabling immediate loading as well as immediate placement (see FIG. 19).

In other words, the implant fixtures B and C are structures that can minimize damage to bones in the horizontal and vertical directions, can be supported in the horizontal direction as much as possible by horizontal lamellar bones, and can leave much of the structurally sound bones in place in the horizontal direction. In particular, the implant fixture C is advantageous for immediate loading. It is difficult for the conventional cylindrical implant to be horizontally supported by bone, which makes it difficult to apply the conventional cylindrical implant to immediate loading. In addition, secondary surgical treatment for connecting a prosthetic tooth to the implanted implant fixture is further needed after waiting for secondary healing of damaged bone. Since the conventional implant fixture is cylindrical and the screw has a very small depth, it provides a low fixing force and has no structure for bearing a vertical load, making it difficult to perform immediate loading and to secure a fixing force for healing.

In contrast, the implant fixture of the present invention has a self-drilling function which leaves only a small hole in lamellar bone. Due to the function, the implant fixtures B, C and D have the same characteristics as disc type implant fixtures although they are implanted downward in the same manner as the conventional cylindrical implant fixtures. A significant portion of the core 51 is structurally removed, but the strength of the core for maintaining the structure of the implant fixture is in harmony with the mechanical structure of the screw lines 52 to improve the strength of the implant fixture. The strength of the implant fixture according to the present invention can be maintained even in the case where the core 51 disappears and only the screw lines 52 are present. This structure is unique to the implant fixture 100 of the present invention and cannot be expected in any conventional implant fixture.

In conclusion, the implant fixture of the present invention enables both immediate placement and immediate loading, which are the most ideal implantation methods.

Figure 6:
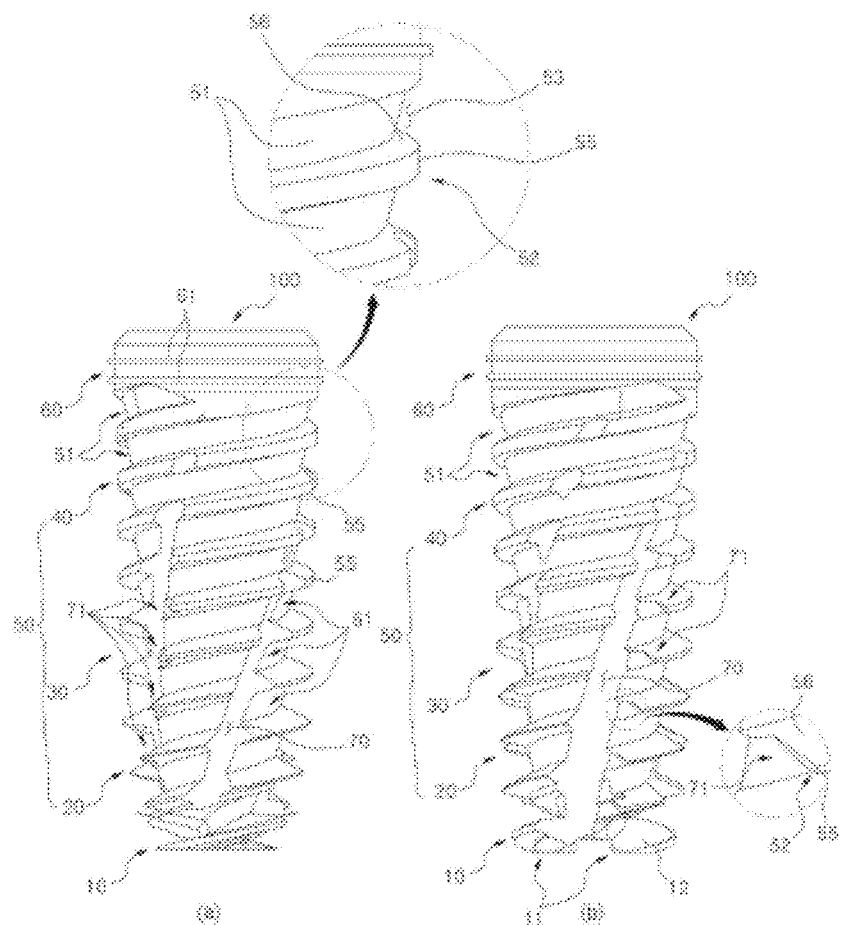
FIG. 6 illustrates a front view and a side view of main portions of an implant fixture of the present invention.
Figure 7:
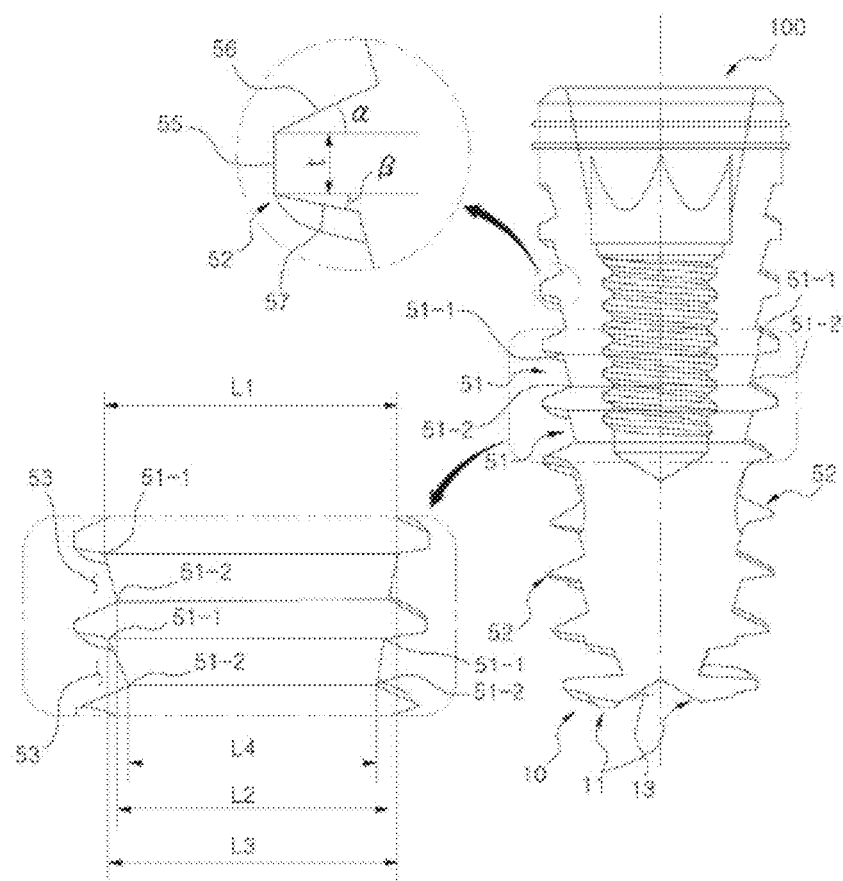
FIG. 7 illustrates detailed views of a core of an implant fixture of the present invention.

The greatest characteristic of the implant fixtures A, A', and B according to the embodiments of the present invention is that the body section 50 includes the valleys 53 and the screw lines 52 whose side surfaces 55 have a gradually increasing thickness in the order of the drilling portion 20, the support portion 30 and the seating portion 40. As illustrated in FIGS. 6 and 7, the body section 50 is broadly divided into the seating portion 40, the support portion 30, and the drilling portion 20. Although this division is not clear, these portions are distinguished according to the shapes of the side surfaces of the screw lines 52. The screw lines 52 spirally protrude from the outer circumferential surface between the valleys 53. The screw lines 52 become increasingly thick downward from the sharp side surfaces 55, which are distal ends of the screw lines 52. As illustrated, the side surfaces of the screw lines 52 formed at the drilling portion 20, which is formed at the lowermost end of the implant fixture 100, are sharp, and have larger thicknesses t at the support portion 30 and the seating portion 40. That is, the drilling portion 20, the support portion 30 and the seating portion 40 constituting the body section 50 are distinguished according to the thicknesses t of the side surfaces 55. The functions of the constituent portions are as follows. The tip section 10 in front of the body section 50 is moved forward in contact with the alveolar bone 1 and slices the bone to form a hole. At this time, the screw lines 52 of the drilling portion 20 follow the tip section 10 and are fitted into the hole 2 of the alveolar bone 1 formed by the tip section 10. The screw lines 52 follow the tip section 10 providing posterior support for the drilling.

Thereafter, when the tip section 10 advances in fact-to-face contact with the alveolar bone 1 and drills the alveolar bone 1, the support portion 30 at the rear of the drilling portion 20 enters the bone to replace the previous position of the drilling portion 20. The support portion 30 whose side surfaces 55 have the larger thickness t is introduced into the bone, which has been widened by the drilling portion 20. That is, the support portion 30 performs a condensing function. As described above, since the implant fixture 100 of the present invention has a downward tapered shape, the diameter of the implant fixture 100 entering the bone increases. In the end, the tip section 10 of the implant fixture 100 according to the present invention cuts and drills the alveolar bone 1, and the hole 2 of the bone is enlarged by the drilling portion 20, the support portion 30 and the seating portion 40 to achieve firm coupling between the implant fixture and the bone. The insertion of the increasingly large volume into the hole 2 formed in the alveolar bone 1 enlarges the hole and achieves coupling between the implant fixture and the bone, indicating a self-condensing function.

Figure 5:
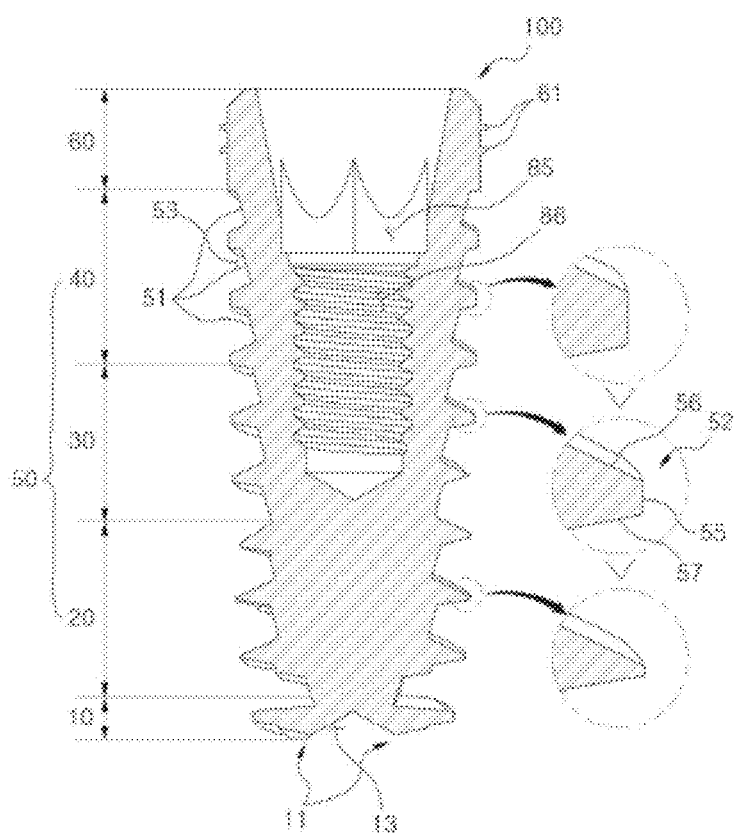
FIG. 5 is a front cross-sectional view illustrating main portions of an implant fixture of the present invention.

As illustrated in the enlarged views of FIGS. 5 and 7, the side surfaces 55 of the support portion 30 are thicker than the side surfaces 55 of the drilling portion 20, and the side surfaces 55 of the seating portion 40 have a larger thickness t than those of the support portion 30. The body section 50 is tapered such that the diameters increase gradually in this order.

In the present invention, the thicknesses t of the side surfaces 55 of the screw lines 52 increase gradually from the bottom to the top, i.e. in the order of the drilling portion 20, the support portion 30, and the seating portion 40. The body section 50 of the implant fixture 100 according to the present invention is divided into the drilling portion 20, the support portion 30, and the seating portion 40. The side surfaces 55 of the drilling portion 20 are smaller in thickness than those of the support portion 30. According to the present invention, the side surfaces 55 of the body section 50 have a gradually increasing diameter in the order of the drilling portion 20, the support portion 30, and the seating portion 40. Each of the drilling portion 20, the support portion 30, and the seating portion 40 may be formed with a plurality of screw lines 52. Even in this case, the side surfaces of the screw lines 52 formed on the drilling portion 20 may have the same thickness, as described above.

More preferably, the side surfaces 55 of the drilling portion 20, the support portion 30, and the seating portion 40 within each portion have different thicknesses t. This configuration is illustrated throughout the drawings. The side surface 55 of the screw line 52 at the lower part of the implant fixture 100 has a smaller thickness t than the side surface 55 of the screw line 52 at the upper part of the implant fixture 100. This is applied to all portions of the body section 50. This embodiment allows for a uniform increase in the pressure applied to the alveolar bone 1 and is convenient to prevent a sudden pressure increase.

In the present invention, the body section 50 includes the valleys 53 and the screw lines 52 whose cross-section has a side surface 55 including a tapered upper end surface 56 and a tapered lower end surface 57. The angle of the tapered upper end surface 56 with respect to the horizontal plane is greater than that of the tapered lower end surface 57 with respect to the horizontal plane.

Figure 8:
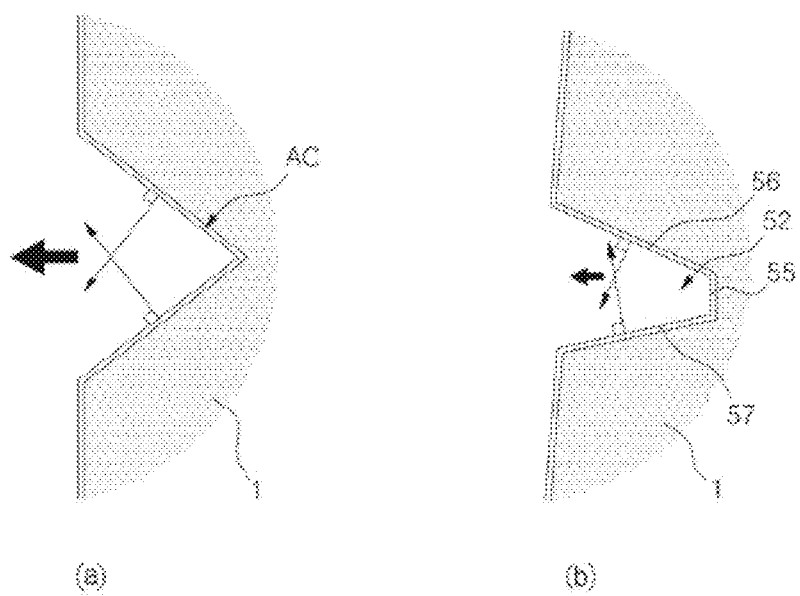
FIG. 8 illustrates the operational mode of a screw line of an implant fixture of the present invention.

This feature is shown in detail in FIGS. 7 and 8. In a cross-sectional view of each of the plural screw lines 52 of the body section 50, the tapered upper end surface 56 is formed at the upper portion of the side surface and the tapered lower end surface 56 is formed at the lower end of the side surface. Each of the screw lines is tapered at different angles. The tapered upper end surface 56 has an angle α and the tapered lower end surface 57 has an angle β with respect to the horizontal plane as illustrated in FIG. 7. The angle α is greater than the angle β.

The reason why this structure is applied to all screw lines 52 is clear. This structure can generate a vertical force that is better tolerated by the bone. FIG. 8 illustrates a relationship between the screw line 52 and the alveolar bone 1 from the standpoint of friction and force when the screw line 52 is rotated in the alveolar bone 1. FIG. 8a illustrates a cross-sectional view of a wedge-shaped screw line 52 generally used in the art, and FIG. 8b illustrates a cross-sectional view of the screw line 52 used in the present invention. As illustrated in FIG. 8a, the screw line in close contact with the bone in a hole formed in the alveolar bone 1 receives forces arising from the friction between the screw line and the bone when the implant fixture is rotated. The screw line always receives forces exerted in the vertical directions relative to the contact portions between the bone and the screw line. In the wedge-shaped screw line 52, the forces delivered from the contact portions are substantially exerted in the horizontal direction. Thus, the screw line receives not only the vertical force but also the horizontal force when the implant fixture 100 is rotated, as illustrated in FIG. 8a. As a result, the forces shake the implant fixture 100 in left and right directions, impeding accurate drilling.

In contrast, the tapered upper end surface 56 of the screw line 52 forms a much larger angle, as illustrated in FIG. 8b. Thus, the vertical forces on the different surfaces are larger in magnitude than the force exerted in the horizontal direction. Consequently, when the implant fixture 10 is rotated, the vertical forces are more exerted than the horizontal force. The fact that the vertical forces are larger than the horizontal force is of great significance in the present invention.

The alveolar bone 1 tends to resist a vertical force very well. However, the alveolar bone 1 is easily destroyed and tends to be broken by a horizontal force. In consideration of this problem, the present invention is designed such that a rotational force applied to the implant fixture 100 can be completely delivered in the vertical direction by imparting a maximum horizontal angle to the screw line 52.

In the present invention, upper and lower angles of the screw are adjusted such that an implantation pressure is delivered as a vertical force during implantation of the implant fixture, and a force delivered to the bone by the implant fixture even during function is delivered as a vertical force after implantation to prevent destruction of the bone. This is a self-force direction conversion system to convert a shear force or transverse force into a vertical force.

In the present invention, when forming each valley 53, the core 51 of the body section 50 is preferably tapered downward such that upper end cores 51-1 have a larger diameter than lower end cores 51-2. That is, as described above, the body section 50 can be divided into the drilling portion 20, the support portion 30, and the seating portion 40 from the bottom according to their locations in the vertical direction. The body section can also be divided into the core 51 and the screw lines 52, as viewed in the horizontal plane. The core 51 is placed within a predetermined range from the central axis and the screw lines 52 surround the core 51.

When the implant fixture 100 of the present invention is viewed from the front or lateral side thereof, the valleys are formed between the screw lines 52 and thus the core 51 is seen between the screw lines 52. As illustrated in FIG. 7, the upper end cores 51-1 refer to upper portions of the core 51 and the lower end cores 51-2 refer to lower portions of the core 51. In the present invention, the core 51 is manufactured to have a downward tapered shape.

Assuming two upper and lower cores 51 divided by the screw line 52 in the vertical direction, the upper core 51 is tapered such that a first upper end core 51-1 and a first lower end core 51-2 have diameters L1, L2, respectively, and the lower core 51 is also tapered such that a second upper end core 51-1 and a second lower end core 51-2 have diameters L3, L4, respectively. The diameters increase in the order of L4<L2<L3<L1.

That is, the two cores 51 are divided in the implant fixture 100, as illustrated in the enlarged views of FIG. 7. The diameter of the core 51 of the conventional wedge-shaped implant fixture 100 linearly decreases at a predetermined angle, whereas the diameter of the inner core 51 inside the valley between the screw lines increases and decreases repeatedly in the implant fixture of the present invention. When a pressure applied to the conventional linear wedge-shaped implant fixture increases continuously, it is excessively applied to the bone during implantation, causing damage to the bone. In contrast, the implant fixture of the present invention is coupled to the alveolar bone 1 by reducing a pressure applied to the alveolar bone 1, gradually increasing the pressure, and reducing the pressure again. This stress buffering and releasing effect prevents an excessive pressure from being delivered to the bone.

An implant fixture (Ostem, Novel Active, Alpha Bio) having a tapered shape as a whole or a middle part protruding pot-shaped implant fixture designed to increase stability inevitably causes an increase in pressure during implantation. In this case, an excessive pressure is delivered to a middle portion, an upper end, or a particular portion according to the situation of the bone. To solve this problem, the implant fixture 100 of the present invention has a tapered shape as a whole and the diameters of the core 51 between the screw lines are adjusted. As illustrated in FIG. 7, the first upper end core 51-1 and the first lower end core 51-2 of the upper core 51 have diameters L1, L2, and the second upper end core 51-1 and the second lower end core 51-2 of the lower core 51 have diameters L3, L4. The diameters increase in the order of L4<L2<L3<L1. As the core 51 penetrates the alveolar bone 1, the diameter of a hole formed in the bone increases from L4 to L3. Subsequently, the core portion having L2 smaller than L3 is introduced into the bone. When the core 51 is further introduced into the bone, the diameter of the hole increases from L3 to L1, which is greater than the diameter L3. In such a stress release manner, the implant fixture 100 of the present invention prevents a pressure from concentrating on a particular portion of the bone during dental surgery.

In more detail, due to the structure in which the diameter and thickness of the screw increases and the diameter of the core 51 increases and decreases in a stepped, circulating, and repeated manner, the present invention can achieve an automatic pressure regulating system that enables a condensing function to densify the bone tissue and to increase stability by pressurization of the bone.

Without this function, implantation faces increased resistance and the increased implantation resistance goes above the necessary fixing force when implantation is forcibly continued, whereby the bone cannot withstand the resistance. As a result, the bone is destroyed and collapses, which is a cause of implant failure. In an attempt to avoid an excessive increase in pressure during implantation, a conventional implant fixture is withdrawn and drilling is performed again or is rotated in the counterclockwise direction to retrieve and is then rotated clockwise to reduce the pressure to some extent. However, this attempt is unsatisfactory in efficiency and has low effectiveness.

However, the present invention provides a function of a back cutting system so that resistance is reduced to a considerable extent when the implant fixture is rotated in the reverse direction and is then rotated clockwise again, making it possible to place the implant fixture with an optimal pressure to obtain anchoring as the bone is reduced during reverse rotation.

Preferably, the body section 50 has any of one to four rows of guide grooves 70 ascending spirally ascending vertically along the outer circumferential surface thereof. For example, one row, two rows, three rows, or four rows of guide grooves 70 may be formed, if needed. The implant fixture 100 of the present invention can be placed after drilling a small hole. It is because the implant fixture 100 has a drilling function and a function to utilize necessary portions of the cut alveolar bone 1 during implantation and discharge unnecessary portions of the alveolar bone. A powder or pieces of the necessary alveolar bone 1 are in the hole between the implant fixture 100 and the alveolar bone 1 without being discharged to outside. The gathered powder or pieces of the alveolar bone 1 will be regenerated into a new alveolar bone. The reason why the bone powder is not discharged outside and is accumulated around the implant fixture 100 is that autologous bone powder is easily to be converted into a new bone. According to the present invention, when the tip section 10 is moved forward to cut the alveolar bone 1, the valleys and the guide grooves 70 formed on the outer circumferential surface of the implant fixture 100 are filled with the sliced or destroyed alveolar bone 1 by the sealing lines 61. The produced bone particles remain along the guide grooves 70 or is discharged outside along the grooves in the initial stage of implantation, but the bone is prevented from being discharged in the late stage of implantation because the sealing lines 61 blocks the guide grooves 70 and the valleys 53. As the implantation proceeds further, dead spaces can be automatically filled by the remaining bone particles by the implantation force.

In a situation where the bone is not good in shape so that the sealing lines 61 cannot cover the bone, the alveolar bone 1 is not discharged to the valleys 53 and the guide grooves 70 of the implant fixture 20 and naturally the bone chips remain in place. That is, the bone filling function is a complex result of the guide grooves, self-drilling, cutting, and sealing.

In each of the conventional implant fixtures, the guide grooves 70 are formed from the bottom to a middle portion, and a large portion of the autologous bone is lost in the course of drilling with a drill as a surgical tool. Further, the drilling function of the tip section 10 is not sufficient, making it difficult to achieve the condensing function and the filling function to accumulate the bone chips around the implant fixture.

In contrast, according to the present invention, the guide grooves 70 substantially transverse the body section 50 in the vertical direction. According to the embodiments of the present invention, one to four guide grooves 70 are formed to prevent a pressure increase during bone cutting, direction change, and condensing and enable condensing and filling with an optimum pressure, leading to improved functionality.

That is to say, the implant fixture of the present invention includes a plurality of guide grooves 70 formed from the tip to the upper portion thereof in order to prevent an excessive increase in pressure due to the condensing and filling functions. The implant fixture of the present invention is designed for an optimum fixing force (high but is not excessive enough to destroy the bone) upon implantation. For example, in a place where the bone is strong and a high pressure is thus required, the implant fixture of the present invention reduces the pressure and resistance by horizontal cutting which will be described later. In a place where the bone is weak and has a low density, the implant fixture of the present invention pressurizes the bone by the condensing function and densifies the bone to increase stability. As a result, an optimum fixing force can always be obtained with an optimum pressure.

Preferably, the screw lines 52 placed at the right sides of each of the guide grooves 70 have cutter portions 71. The cutter portions 71 are formed by cutting the screw line 52.

Implantation resistance can be reduced by varying the direction of the cutting angle to increase the cutting range and cutting diversity, ensuring proper cutting under various environments. The implant fixture 100 is rotated and inserted forward cutting the bone that it faces with the tip section 10. The drilling portion 20 following the tip section 10 is larger in diameter and thickness than the tip section 10. When the portion is inserted into the hole of the alveolar bone 1 created by the tip section 10, there is a risk that the rotating force may be lowered. Thus, the cutter portions 71 formed at the right sides of the screw lines 52 of the implant fixture 100 cuts the alveolar bone. The cutter portions 71 induce forward movement of the implant fixture while rotating to the right sides of the guide grooves 70, that is, in the clockwise direction. From the frontal view of the implant fixture in the drawings, the cutter portions 71 are formed by cutting the screw lines 52 placed at the right sides of the guide grooves 70.

Figure 9:
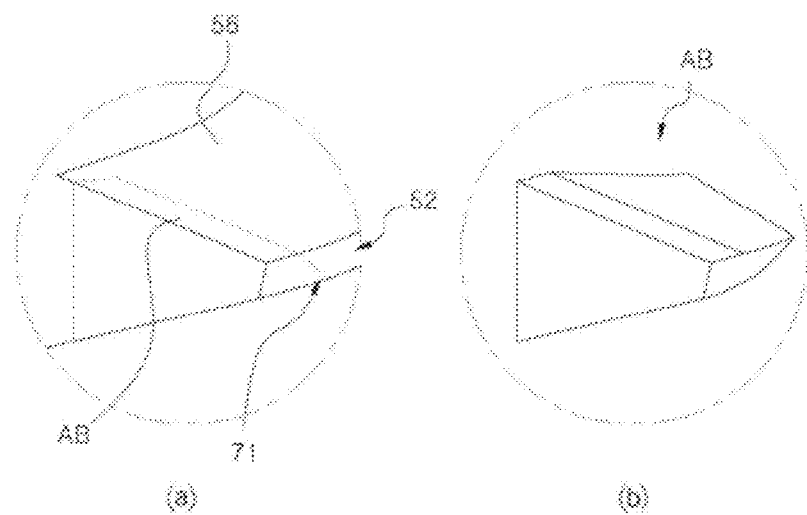
FIG. 9 illustrates the shape of a cutter portion formed in a screw line of an implant fixture of the present invention.
Figure 10:
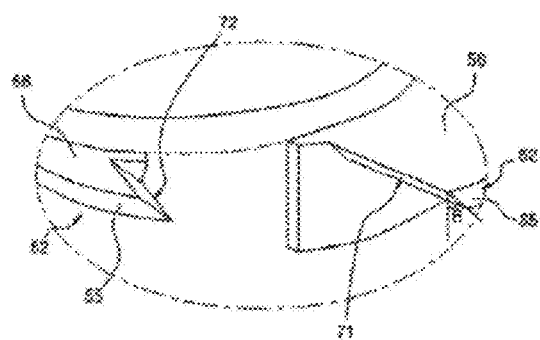
FIG. 10 illustrates the shapes of a cutter portion and a counterpart cutter portion formed in a screw line of an implant fixture of the present invention.

FIGS. 9 and 10 illustrate more detailed embodiments of the present invention. Preferably, the cutter portion 71 is tapered downward to the right side by cutting the screw line downward to the right side. That is, when forming the cutter portion 71, the screw line 52 is cut such that the right side is tapered and a portion of the screw line 52 that comes in contact with the alveolar bone 1 acts as a cutter when the implant fixture is rotated clockwise. Thus, the alveolar bone 1 can be cut laterally by a cutter blade (which is also present in the conventional implant) naturally formed by the groove and another cutter blade with different angles formed by the cutter portion 71 of the screw line 52 when the implantation direction is changed. This is intended to freely change the implantation direction to forward, backward, left, and right directions while enhancing the function to cut the alveolar bone laterally. That is, the implant fixture 20 is rotated in the clockwise direction (or in the forward direction) upon implantation, but the implantation direction can be changed by the cutter portions 71 formed at various angles to cut the bone in forward, backward, left, and right directions. Specifically, as illustrated in FIGS. 9 and 10, the cutter portion is tapered to the right by cutting a portion of the screw line 52 such that a cut portion AB of the screw line becomes sharp rightward.

Figure 11:
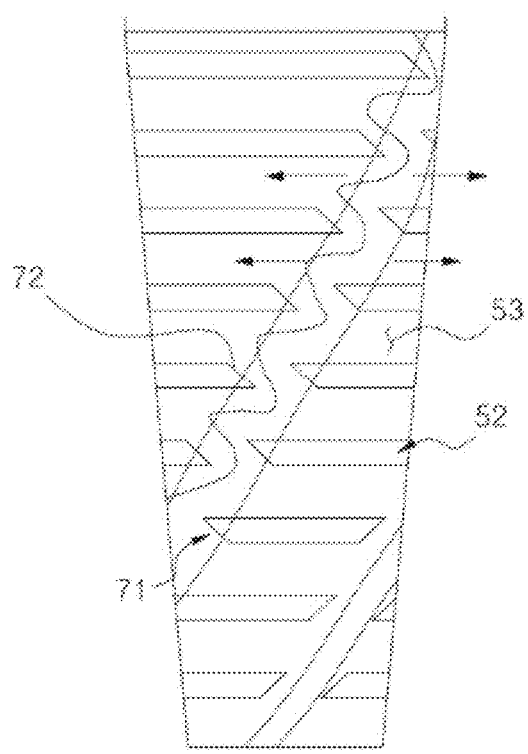
FIG. 11 illustrates a state in which a bone is transported along a guide groove of an implant fixture of the present invention.

As illustrated in FIGS. 9 and 10, the screw line 52 placed at the left side of the guide groove 70 is formed with a counterpart cutter portion 72. The counterpart cutter portion 72 is formed by cutting the screw line 52 upward to the left side. In the conventional implant fixture 100, the bone can be cut by the guide grooves 70 and the cut screw lines 52 not only when the implant fixture is rotated in the clockwise direction to insert the implant fixture to the bone, but when the implant fixture is rotated in the counterclockwise direction to untighten the implant fixture. The counterpart cutter portion 72 corresponding to the cutter portion 71 is formed in the screw line 52 placed at the left side of the guide groove 70. The operation of the cutter portions is illustrated in FIG. 11.

This is the function of the back cutting system of the present invention. Since the bone is cut during reverse rotation of the implant fixture, implantation resistance is greatly reduced when the implant fixture is again rotated in the clockwise direction after the reverse direction. As a result, the implant fixture can be implanted with an optimum pressure by which a desirable stability can be obtained.

In addition, the cut bone, which has been raised along the guide grooves 70, is again pressed downward and is accumulated by the cutter portions 71 and the counterpart cutter portions 72 formed at the right and left sides of the guide grooves 70. The bone chips pressed downward while being raised, and accumulated by the cutter portions 71 can be easily converted into a new bone.

According to the present invention, it is preferred to form the cutter portions 71 or the counterpart portions 72 in the drilling portion 20 and the support portion 30, which directly participate in cutting. The cutter portions 71 are not formed in the seating portion 40. The cutter portions 71 and the counterpart cutter portions 72 along the tip section 10, the drilling section and the support section can cut a necessary region of a narrow bone and improve the drilling function and the horizontal cutting function of the implant fixture 100. In addition, when the implant fixture is erroneously implanted, the cutter portions 71 and the counterpart cutter portions 72 effectively assist in re-implanting and correcting the implant fixture in a correct direction.

Preferably, the cutter portion 71 or the counterpart cutter portion 72 has one or two rows of guide grooves 90.

Figure 12:
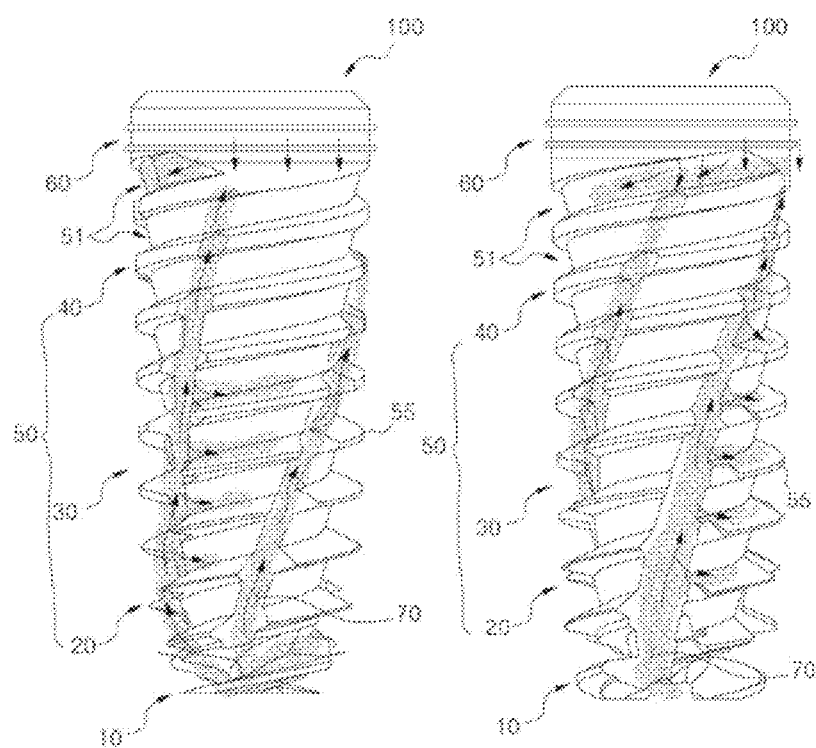
FIG. 12 illustrates a state in which a bone is moved along and filled in guide grooves of an implant fixture of the present invention.
Figure 13A:
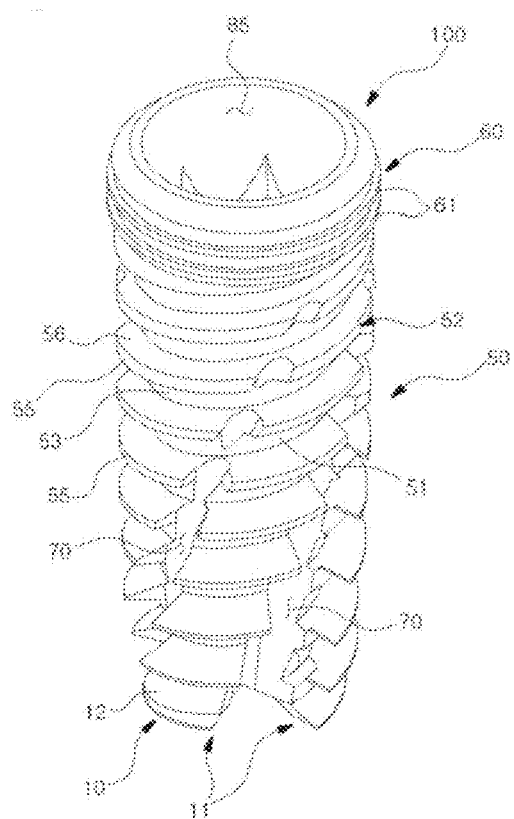
FIG. 13a is a perspective view illustrating an implant fixture A of the present invention.
Figure 13B:
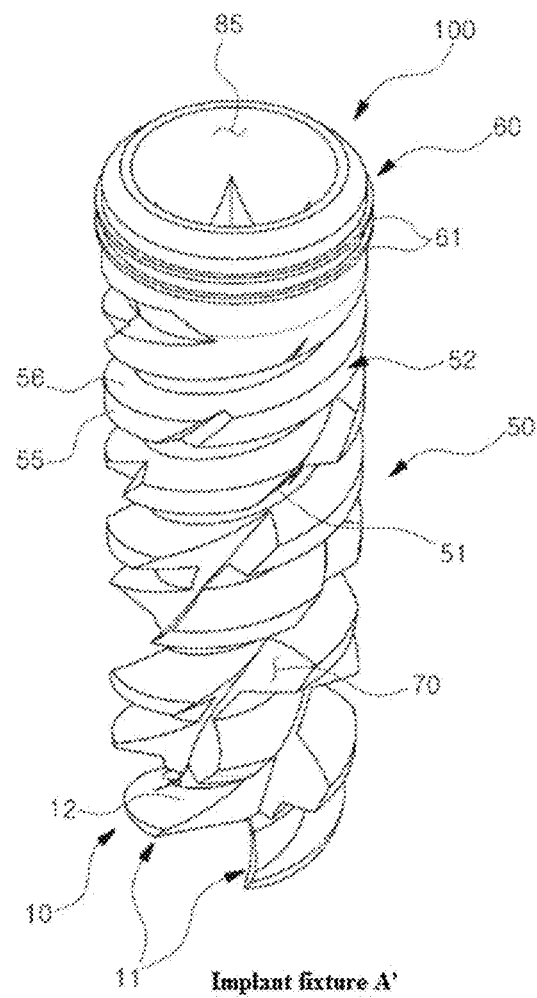
FIG. 13b is a perspective view illustrating an implant fixture A' of the present invention.
Figure 13C:
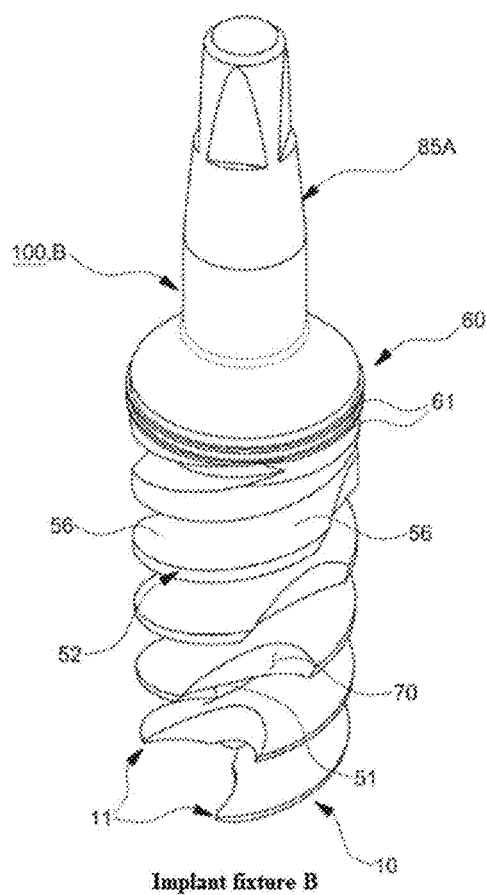
FIG. 13c is a perspective view illustrating an implant fixture B of the present invention.
Figure 13D:
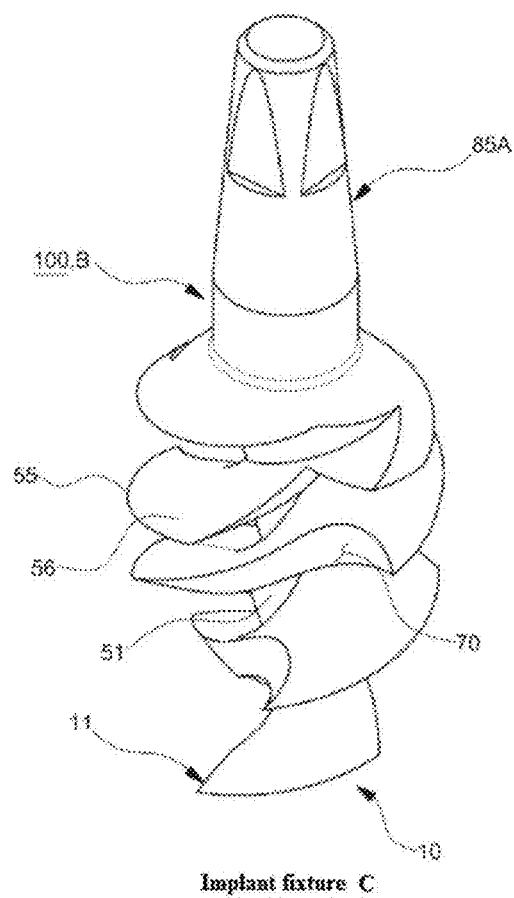
FIG. 13d is a perspective view illustrating an implant fixture C of the present invention.
Figure 13E:
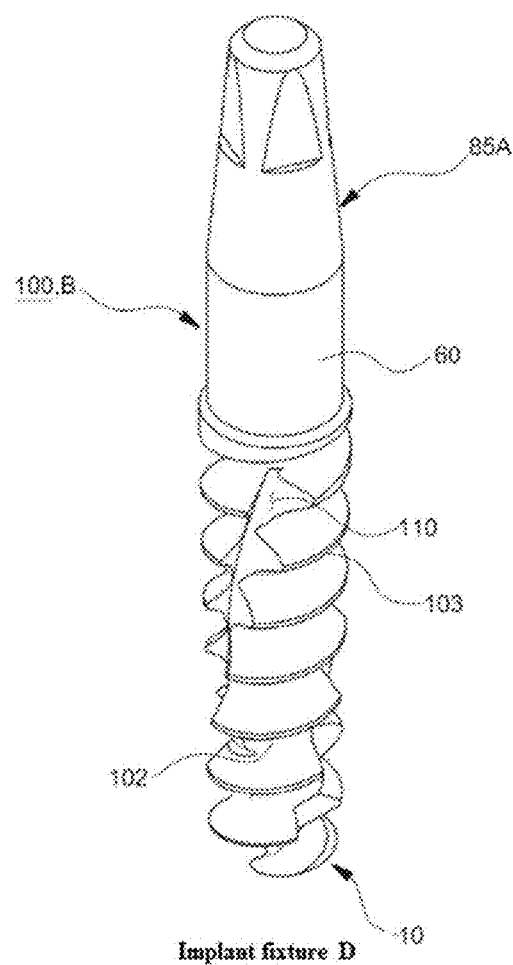
FIG. 13e is a perspective view illustrating an implant fixture D of the present invention.
Figure 14A:
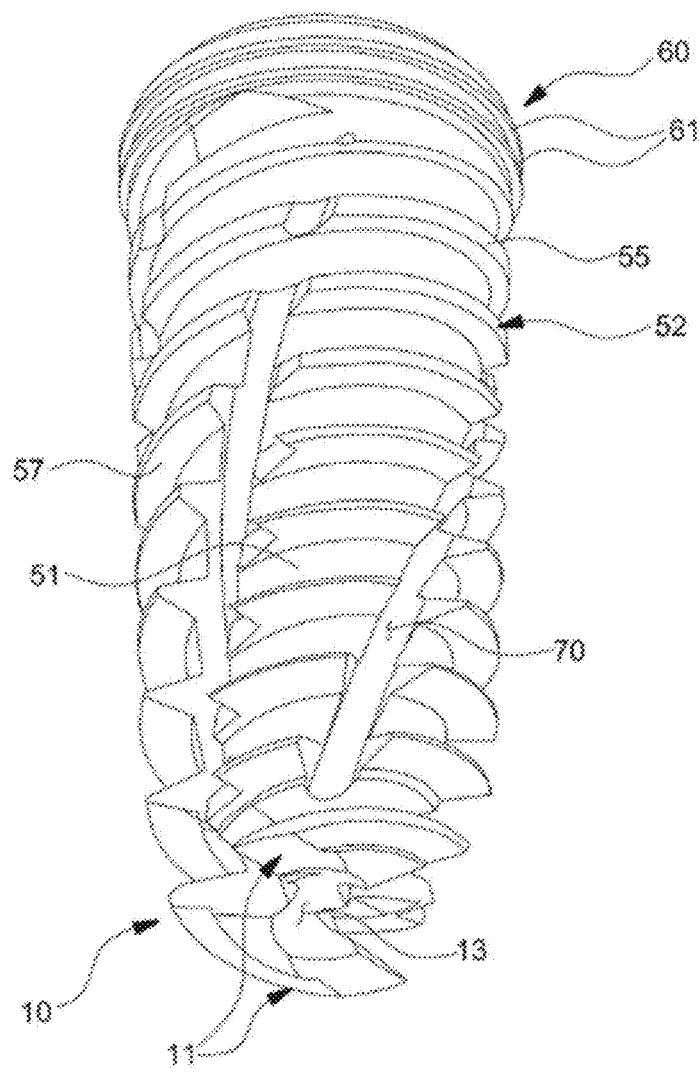
FIG. 14a is a bottom perspective view illustrating an implant fixture A of the present invention when viewed from a tip section of the implant fixture A.
Figure 14B:
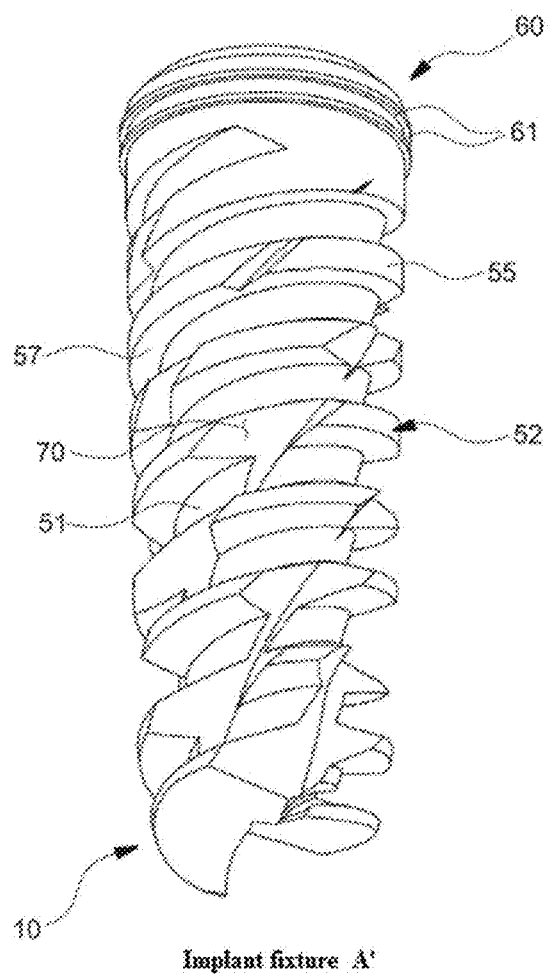
FIG. 14b is a bottom perspective view illustrating an implant fixture A' of the present invention when viewed from a tip section of the implant fixture A'.
Figure 14C:
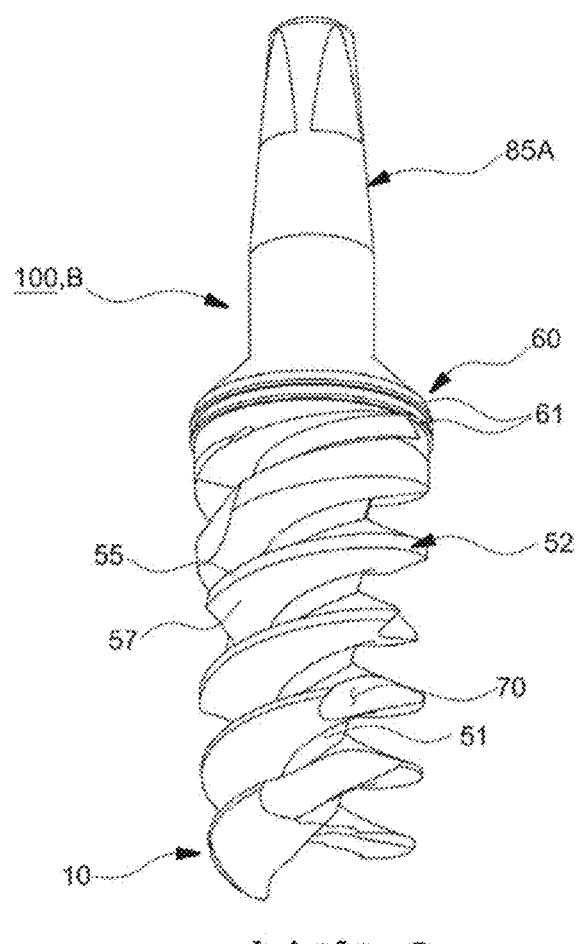
FIG. 14c is a bottom perspective view illustrating an implant fixture B of the present invention when viewed from a tip section of the implant fixture B.
Figure 14D:
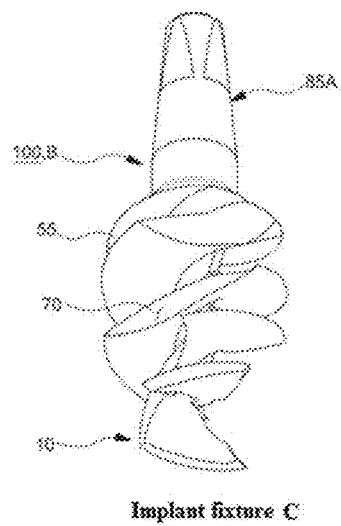
FIG. 14d is a bottom perspective view illustrating an implant fixture C of the present invention when viewed from a tip section of the implant fixture C.
Figure 14E:
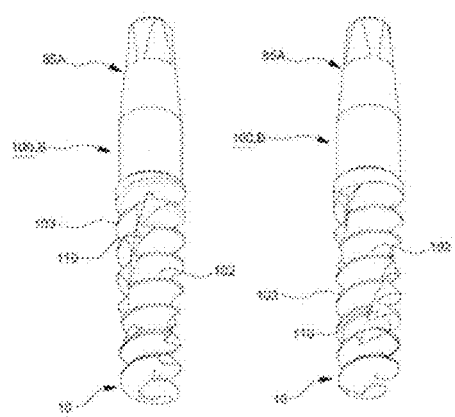
FIG. 14e is a bottom perspective view illustrating an implant fixture D of the present invention when viewed from a tip section of the implant fixture D.
Figure 15:
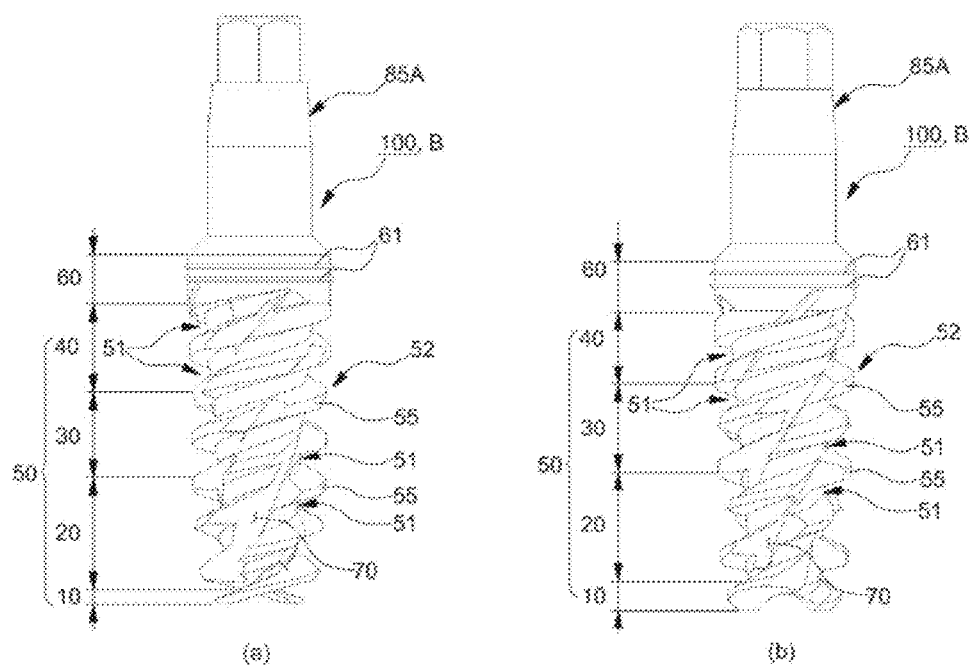
FIG. 15 illustrates front views of an implant fixture B of the present invention.

As described above, three or four rows of guide grooves 70 are formed in the vertical direction of the body section 50. Preferably, only one or two rows of guide grooves 70 are formed at predetermined intervals rather than the cutter portions 71 are formed in all guide grooves. If the cutter portions 71 capable of cutting the bone while rotating are formed in all guide grooves 70, the alveolar bone 1 may be excessively cut into pieces. Thus, the cutter portions 71 are formed only in one or two rows of the guide grooves 70 to enhance the drilling, condensing, and correcting drilling mistakes of the implant fixture. For better explanation of such operation, the moving directions of chopped or cut pieces of the alveolar bone 1 are shown in FIG. 12.

The drilling function is the most important function of the implant fixture 100 according to the present invention. The drilling function is achieved by the propeller type tip section 10 as described before. The tip section 10 continuously performs horizontal cutting of the alveolar bone 1 while rotating to form a vertical hole in the bone. The body of the implant fixture is moved forward by the tip section 10. This operation can be achieved by the tip section 10 having a structural space, which is formed by cutting a central portion of the lower end of the core. The tip section 10 may be formed with a concave recess 13 or may have a propeller shape.

First, the propeller shape of the tip section 10 is advantageous for horizontal cutting and vertical drilling of the alveolar bone 1. Specifically, the propeller shape of the tip section 10 is obtained by forming the guide grooves 70 in a spiral shape having a predetermined angle and a diameter less than or equal to that of the screw valley while surrounding the central portion of the core, and completely removing portions of the core 51 outside the spiral guide grooves 71 underlying the first screw line and not included in the spiral guide grooves 71 (see the implant fixture A' of FIG. 4b and the implant fixture A' of (b) in FIG. 4c).

Figure 4C:
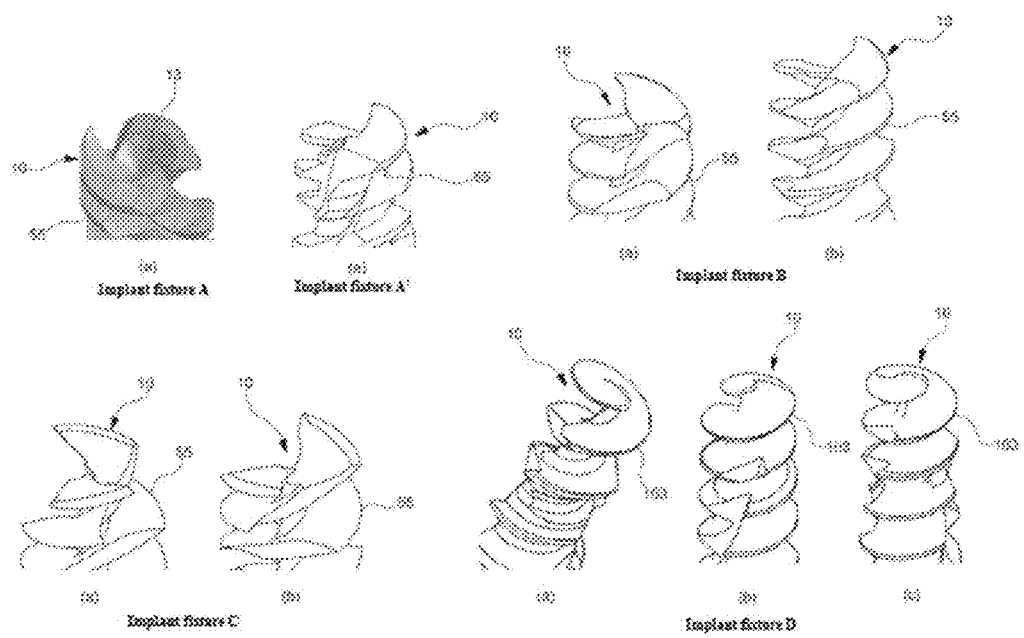
FIG. 4c illustrates tip sections of implant fixtures according to embodiments of the present invention.

Second, the concave recess 13 of the tip section 10 may be formed at a lower central portion of the core 51 of the tip section 10 (see the implant fixture A of FIG. 4b and the implant fixture A of (a) in FIG. 4c). The propeller shape defined by the guide grooves 70 or the concave recess 13 is needed in order to realize a self-drilling function by which the implant fixture penetrates the bone to form the hole 2 therein. The conventional implant fixture 100 including a flat or convex tip has no substantial function to vertically penetrate the bone. The convex tip is necessarily structured to destroy the alveolar bone 1 while moving forward when it is intended to drill the alveolar bone 1. This structure is not suited to a slice cutting mode that induces less bone destruction. Further, this structure may involve pain and delay regeneration of the alveolar bone 1.

In the present invention, the concave recess 13 formed at the lower end of the center of the core 51 or the propeller shape of the core 51 realizes the self-drilling function. The tip section 10 slices the alveolar bone 1 upon contact with the bone to form a hole therein and a portion of the alveolar bone 1 accommodated in the concave recess 13 is also cut thin to form a hole. According to the present invention, the concave recess 13 may have various shapes, for example, circular (a), diamond-like, triangular (f), quadrangular (d), pentagonal, hexagonal (b), octagonal (c), star-like (e), star-like (hexagonal), and star-like (octagonal) shapes. According to the present invention, the tip section 10 provides not only a drilling function of the implant fixture 100 but also a direction correction function of the implant fixture 100.

Preferably, the tip section 10 includes one to four cutting tips 11. When the tip section 10 has a propeller shape, the cutting tips 11 acting as blades may be arranged at uniform intervals. The presence of a greater number of cutting tips 11 in the tip section 10 increases the danger that the cutting tips 11 can be broken by friction with the alveolar bone 1. Meanwhile, the presence of few cutting tips 11 in the tip section is undesirable because of negligible drilling effect. In addition, each of the cutting tips 11 may have a tip cutter portion 12. The tip cutter portion 12 is formed by tapering the upper end of the cutting tip 11 in the clockwise direction. The alveolar bone 1 faced by the cutting tips 11 is cut in thick slices but is cut thin by the tip cutter portion 12 to form a hole.

When the cutting tips 11 are brought into face-to-face contact with the alveolar bone 1 and the implant fixture is rotated, the tip cutter portions 12 cut the alveolar bone 1 into slices, like paring an apple, to form a hole.

The overall constitution of the implant fixture 100 according to the present invention and the implant fixtures A, A', B, and C have been described above. The implant fixture D also has characteristics in that the tip section 10 has a unique structure, as illustrated in (d) of FIG. 4a and (e) in 4b. The implant fixture 100 has a downward tapered or reverse-tapered shape and formed with a screw on the outer circumferential surface thereof. Specifically, the implant fixture 100 includes a tip section 10 at the bottom for directly drilling the alveolar bone 1 of a tooth; a body section 120 including a core 102 integrally formed with the upper end of the tip section 10 and acting as a central shaft, and one row of screw lines 103 spirally formed along the outer circumferential surface of the core 102 such that the alveolar bone 1 is cut and drilled through screw rotation; a connection section 60 ascending from the upper end of the body section 60 to have a circular outer circumferential surface; and a tooth engaging section 85A extending from the upper end of the connection section 60 to be directly connected to a tooth. Thus, the tip section 10 is formed such that a portion of the core 102 at a distal end of the tip section 10 is removed and the distal ends of the one row of spiral screw lines 103 are located concentrically at predetermined distances from the center-line and the screw lines 103 have downward tapered outer circumferential surfaces.

That is, as illustrated in (d) of FIG. 4a, (e) of FIG. 4b, or FIG. 16, this embodiment has an integral shape, which corresponds to the one-body type implant fixture 100,B. The one row of screw lines 103 is spirally formed around the outer circumferential surface of the body section 120. In the tip section 10, the screw lines 103 are formed to surround the core 102 starting from a slightly eccentric location from the center-line.

Although this embodiment has the same drilling function as in the implant fixture 100 having the propeller type tip section 10, its tip section 10 has a different structure from the propeller type tip section. In this embodiment, the tip section 10 has one cutting blade, as illustrated in (e) of FIG. 4b and FIG. 4c. That is, the tip section 10 is formed by slightly modifying the propeller type tip section such that the core 102, which is a central portion of the tip section 10, is removed to leave a space. The screw lines 52 formed in the body section 120 extend to the tip section 10 and are twisted in a downward tapered spiral structure, like a screw. Only distal ends of the screw lines 103 perform a cutting function, but the cutting portion continuously performs horizontal cutting while rotating at the upper end of the alveolar bone to form a hole in the vertical direction and move the body of the implant fixture forward.

The single screw type tip section 10 may be formed with a single guide groove 120, unlike the propeller type tip section 10. In addition, the cutting portion formed in the single screw type tip section 10 may be inclined downward so as to penetrate into the horizontal plane (i.e. the alveolar bone 1) during procedure, like the implant fixtures A, A', B, and C as described before. The main technical feature of the tip section 10 of the implant fixture according to the present invention is that the core 102 is removed from the tip section 10 and the cutting portion is brought into slant contact with the alveolar bone 1 in both the propeller type and the single screw type tip sections. When the implant fixture penetrates into the alveolar bone 1, the propeller type tip section 10, it advances while the tip section 10 having the concave recess, or the single screw type tip section 10 in face-to-face contact with the alveolar bone 1 cuts the contact portion of the alveolar bone 1 into slices without destroying the alveolar bone 1.

All five embodiments illustrated in FIG. 4b have been described above.

A brief explanation will be given of the implant fixtures B and C. First, the implant fixture B is formed with a screw on the outer circumferential surface thereof. The implant fixture B includes a tip section 10 at the bottom for directly drilling the alveolar bone 1 of a tooth; a body section 50 including a drilling portion 20 formed at the upper end of the tip section 10, a support portion 30 formed at the upper end of the drilling portion 20, and a seating portion 40 formed at the upper end of the support portion 30, these portions being formed integrally and each thereof including a core 51 acting as a shaft and screw lines 52 spirally protruding from the outer circumferential surface of the core 51; a connection section 60 formed at the upper end of the seating portion 40 to have a vertical cylindrical shape; and a tooth engaging section 85A extending from the upper end of the connection section 60 and engaged with the tooth. The implant fixture is of an integral one-body type.

This embodiment is illustrated in (c) of FIG. 4b. The implant fixture has been described previously, and thus a detailed description thereof will be omitted.

The implant fixture C illustrated in (d) of FIG. 4b is formed with a screw on the outer circumferential surface thereof. The implant fixture C includes a tip section 10 at the bottom for directly drilling the alveolar bone 1 of a tooth; a body section 50 including a drilling portion 20 formed at the upper end of the tip section 10, a support portion 30 formed at the upper end of the drilling portion 20, and a seating portion 40 formed at the upper end of the support portion 30, these portions being formed integrally and each thereof including the core 51 acting as a shaft and screw lines 52 spirally protruding from the outer circumferential surface of the core 51; a connection section 60 formed at the upper end of the seating portion 40 to have a vertical cylindrical shape; and a tooth engaging section 85A extending from the upper end of the connection section 60 and engaged with the tooth. The implant fixture C is of an integral one-body type.

In the one-body type implant fixture C, the core 51 is preferably formed as a line proximate to the center-line CL of the one-body type implant fixture C and having a thickness of 0.01 mm to 0.5 mm when the screw lines 52 are formed.

Finally, important features of the present invention will be described. The propeller type tip for a drilling function at a tip end of the implant fixture is very important for primary stability as well as implantation depth adjustment and direction change. When the implant fixture is rotated to cut the structurally sound bone and is stuck, the implant fixture is held in tight contact with and is embedded in the bone. That is, the implant fixture acts like an anchor, achieving firm stability. When the bone quality is poor, an implant fixture having a convex tip must be fixed to the bone only by the tip. If the amount of the bone is small, it is difficult to obtain satisfactory anchoring by the tip alone. An implant fixture having a planar tip can be fixed to the bone by embedding a screw blade laterally in the bone, whereas the screw type of the present invention is very advantageous for primary stability because the screw blade is embedded downward as well as laterally in the bone.

In comparison with the conventional implant fixtures, the implant fixture of the present invention can obtain a high primary stability to achieve a high implant success rate even in an extraction socket and with poor bone quantity or quality, as well as in a normal bone. The implant fixture of the present invention can be placed in bones whose quantity and quality are not sufficient, where surgery has been difficult or impossible to perform.

When an important anatomical structure is positioned close to a portion where the implant fixture is to be implanted, for example, when important nerves or blood vessels are positioned 11 mm deep from the surface of an alveolar bone and the implant fixture is 10 mm long, it is difficult to accurately drill the bone by a depth of 10 mm, posing a high risk of damage to the nerves or blood vessels.

In contrast, due to its self-drilling function, the implant fixture with a length of 10 mm according to the present invention can be accurately implanted 10 mm or 9 mm deep by drilling the bone by about 5 mm depth and slowly inserting at a speed of 20 rpm. Therefore, the implant fixture of the present invention can greatly reduce the risk involved with surgery.

Further, the implant fixture of the present invention may be connected to a prosthetic tooth in various manners. Both external hex system or an internal hex system may be employed. A submerged system, an ITI method, or one body type can also be used without limitation. Particularly, the implant fixtures C and D may be immediately placed and immediately loaded, because there is no or much lower destruction of lamellar bones during drilling when compared to the conventional implant fixtures.

INDUSTRIAL APPLICABILITY

The dental implant fixture of the present invention has a vertical self-drilling function enabling vertical penetration, achieving high primary stability. In addition, the dental implant fixture of the present invention allows immediate loading.

LIST OF REFERENCE NUMERALS

10: Tip section
20: Drilling portion
30: Support portion
40: Seating portion
51: Core
52: Screw lines

What is claimed is:

1. A dental implant fixture having a tapered shape and formed with a screw on an outer circumferential surface thereof, the dental implant fixture comprising:
   a propeller type tip section whose lower central portion is removed such that the alveolar bone of a tooth is directly drilled from a lower end of the tip section;
   a body section integrally formed with an upper end of the tip section and having screw lines spirally protruding from the outer circumferential surface of a center core; and
   a tooth connection section disposed at an upper end of a seating portion extending from the body section,
   wherein valleys of a core of the body section are tapered downward such that upper end cores have a greater diameter than lower end cores, such that where the core consists of two upper and lower cores divided by the screw line in a vertical direction, the upper core is tapered such that a first upper end core and a first lower end core have different diameters, L1 and L2 respectively, the lower core being tapered such that a second upper end core and a second lower end core have different diameters, L3 and L4 respectively, and the diameters increase in the order of L4<L3<L2<L1,
   wherein the body section has any of one to four rows of guide grooves spirally ascending vertically along the outer circumferential surface thereof, and
   wherein the screw lines formed at right sides of the guide grooves are cut to form cutter portions.

2. The dental implant fixture according to claim 1, wherein the body section is an integral body comprising a drilling portion formed at the upper end of the tip section, a support portion formed at the upper end of the drilling portion, and a seating portion formed at the upper end of the support portion, each of the portions comprising the core acting as a shaft and the screw lines spirally protruding from the outer circumferential surface of the core.

3. The dental implant fixture according to claim 1, wherein the tooth connecting section forms a two-body type implant fixture A having spaces concavely recessed in the downward direction and engaged with a prosthetic tooth, or forms a one-body type implant fixture B having a tooth engaging section straightly extending upward from the upper portion of the tooth connecting section.

4. The dental implant fixture according to claim 3, wherein each of the one-body type implant fixture B and the two-body type implant fixture A is formed with sealing lines circumferentially protruding from a cylindrical outer circumferential surface of the tooth connecting section.

5. The dental implant fixture according to claim 3, wherein the body section comprises screw lines and valleys, each of the screw lines has a cross-section that forms a side surface comprising a tapered upper end surface and a tapered lower end surface, and the tapered upper end surface forms a larger angle with respect to the horizontal plane than the tapered lower end surface.

6. The dental implant fixture according to claim 1, wherein the screw lines of the body section are of a single line type in which one spiral screw line protruding from an outer circumferential surface of the center core is spirally rotated, or are of a multiple line type in which a plurality of spiral screw lines protruding from the outer circumferential surface of the center core is spirally rotated.

7. The dental implant fixture according to claim 1, wherein each of the cutter portions is tapered by cutting the screw line downward to the right side.

8. The dental implant fixture according to claim 7, wherein the cutter portions or the counterpart cutter portions are formed in the drilling portion and the support portion.

9. The dental implant fixture according to claim 7, wherein the cutter portions or the counterpart cutter portions are formed in one or two rows of guide grooves.

10. The dental implant fixture according to claim 1, wherein the screw lines formed at left sides of the guide grooves are cut upward to the left side to form counterpart cutter portions.

11. The dental implant fixture according to claim 10, wherein the cutter portions or the counterpart cutter portions are formed in the drilling portion and the support portion.

12. The dental implant fixture according to claim 1, wherein the cutter portions or the counterpart cutter portions are formed in one or two rows of guide grooves.

13. The dental implant fixture according to claim 1, wherein the tip section is manufactured in the form of a propeller to penetrate vertically downward and the core beneath a first screw line is removed for horizontal cutting.

14. The dental implant fixture according to claim 1, wherein a lower center core of the tip section has a recess for additional cutting.

15. The dental implant fixture according to claim 14, wherein the recess is formed at the center of a bottom surface of the tip section and has a circular (a), polygonal, thunderbolt-like, or star shape (e).

16. The dental implant fixture according to claim 15, wherein each of the cutting tips has a tip cutter portion formed by tapering the upper end of the cutting tip in the clockwise direction.

17. The dental implant fixture according to claim 14, wherein the tip section has one to four cutting tips.

18. The dental implant fixture according to claim 1, wherein the body section comprises the screw lines and valleys, and the screw lines have side surfaces whose thicknesses gradually increase in the order of the drilling portion, the support portion and the seating portion.

19. The dental implant fixture according to claim 18, wherein the thicknesses of a side surfaces of the screw lines increase gradually in the upward direction in each of the drilling portion, the support portion, and the seating portion.

* * * * *